United States Patent
Gascón Jiménez et al.

(10) Patent No.: US 10,752,881 B2
(45) Date of Patent: Aug. 25, 2020

(54) TRANS-DIFFERENTIATION OF DIFFERENTIATION CELLS

(71) Applicant: Helmholtz Zentrum München-Deutsches Forschungszentrum für Gesundheit Und Umwelt (GMBH), Neuherberg (DE)

(72) Inventors: Sergio Gascón Jiménez, München (DE); Magdalena Götz, München (DE)

(73) Assignee: Helmholtz Zentrum München—Deutsches Forschungszentrum Für Gesundheit Und Umwelt (GMBH), Neuherberg (DE)

( * ) Notice: Subject to any disclaimer, the term of this patent is extended or adjusted under 35 U.S.C. 154(b) by 66 days.

(21) Appl. No.: 15/113,132

(22) PCT Filed: Jan. 29, 2015

(86) PCT No.: PCT/EP2015/051848
§ 371 (c)(1),
(2) Date: Jul. 21, 2016

(87) PCT Pub. No.: WO2015/114059
PCT Pub. Date: Aug. 6, 2015

(65) Prior Publication Data
US 2017/0002316 A1 Jan. 5, 2017

(30) Foreign Application Priority Data
Jan. 29, 2014 (EP) .................... 14153104

(51) Int. Cl.
*C12N 5/00* (2006.01)
*C12N 5/0793* (2010.01)
*C12N 5/077* (2010.01)
*G01N 33/50* (2006.01)

(52) U.S. Cl.
CPC ......... *C12N 5/0619* (2013.01); *C12N 5/0658* (2013.01); *G01N 33/5091* (2013.01); *C12N 2500/38* (2013.01); *C12N 2501/48* (2013.01); *C12N 2506/08* (2013.01); *C12N 2506/1307* (2013.01); *C12N 2510/00* (2013.01); *G01N 2800/10* (2013.01); *G01N 2800/28* (2013.01)

(58) Field of Classification Search
CPC .................... C12N 5/0619; C12N 2506/1307
See application file for complete search history.

(56) References Cited

U.S. PATENT DOCUMENTS

| 7,732,203 B2 * | 6/2010 | Suh ...................... C12N 5/0619 424/93.2 |
| 2012/0220034 A1 * | 8/2012 | Ahlfors ................ C12N 5/0657 435/375 |
| 2016/0273047 A1 * | 9/2016 | Garc A Puche ..... C12Q 1/6886 |

FOREIGN PATENT DOCUMENTS

| WO | WO-2009149956 A2 | 12/2009 |
| WO | WO-2010111422 A2 | 9/2010 |
| WO | WO-2013177228 A1 | 11/2013 |

OTHER PUBLICATIONS

Deng et al., "Mono- and multisite phosphorylation enhances Bcl2's antiapoptotic function and inhibition of cell cycle entry functions," PNAS, 101(1):153-8 (2004).
International Search Report and Written Opinion issued by the International Searching Authority, dated May 18, 2015, in corresponding International Application No. PCT/EP2015/051848.
Kellner et al., "Transcriptional regulation of the Oct 4 gene, a master gene for pluripotency," Histol Histopathol, 25(3):405-412 (2010).
Fu et al., "Regenerative medicine: transdifferentiation in vivo," Cell Res, 24(2): 141-142 (2014).
Chao et al., "BCL-2 Family: Regulators of Cell Death," Annu Rev Immunol, 16:395-419 (1998).
Kanazawa et al.,"Role of Anti-Apoptotic Gene BCL-2 in Hepatocytic Transdifferentiation Process of Pancreatic Cells," Hepatohogy, 42(4):746A (2005).
Lekstrom-Himes et al., "Biological Role of te CCAAT/Enhancer-binding Protein Family of Transcription Factors," J Biol Chem, 273(44):28545-28548 (1998).
Kanazawa et al., Study on apoptosis-related gene in transdifferentiation of pancreatic cells into liver cells, Liver (2005) V46 (Suppl. 2), p. A465. (Abstract translated into English).
Angelucci et al., "Neuroendocrine Transdifferentiation Induced by VPA is Mediated by PPAR(gamma)Activation and Confers Resistance to Antiblastic Therapy in Prostate Carcinoma," The Prostate, 68:588-598 (2008).
Connell et al., "Therapeutic Transdifferentiation: A novel Approach for Ischemic Syndromes," MDCVJ, 11(3):176-180 (2015).
Gascon et al., "Identification and Successful Negotiation of a Metabolic Checkpoint in Direct Neuronal Reprogramming," Cell Stem Cell, 18(3):396-409 (2016).
Ryan et al., "Dose-dependent effects of vitamin D on transdifferentiation of skeletal muscle cells to adipose cells," J Endocrinology, 217(1):45-58 (2013).

* cited by examiner

*Primary Examiner* — Marcia S Noble
(74) *Attorney, Agent, or Firm* — Foley Hoag LLP

(57) ABSTRACT

The present invention comprises methods and compositions related to trans-differentiating differentiated cells, the methods comprising bringing said cells into contact with a polypeptide or a nucleic acid encoding said polypeptide.

Figure 1:
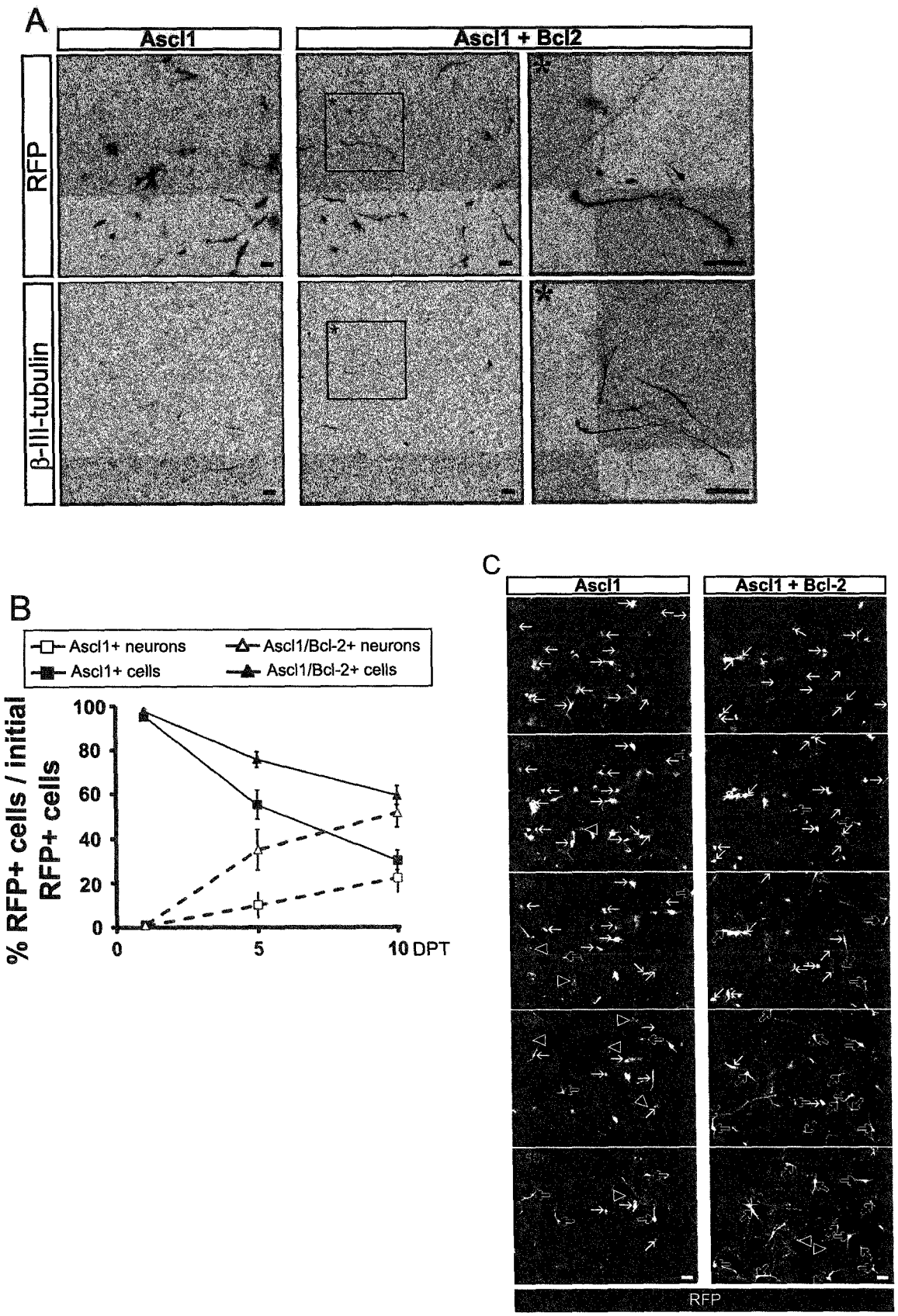
Figure 1:
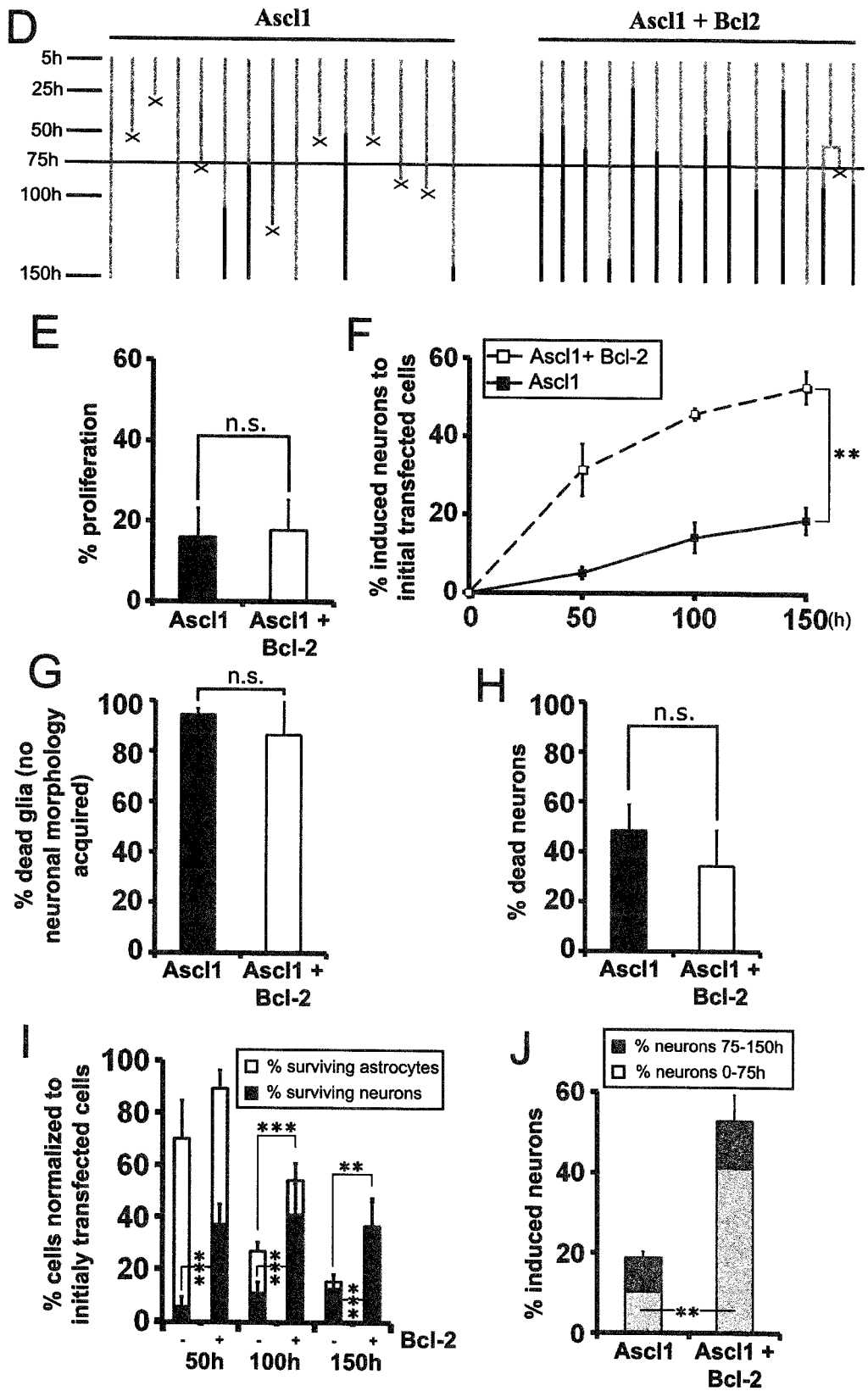

8 Claims, 16 Drawing Sheets
Specification includes a Sequence Listing.

D

SEQUENCE LISTING

<160> NUMBER OF SEQ ID NOS: 21

<210> SEQ ID NO 1
<211> LENGTH: 239
<212> TYPE: PRT
<213> ORGANISM: Homo sapiens

<400> SEQUENCE: 1

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 2
<211> LENGTH: 192
<212> TYPE: PRT
<213> ORGANISM: Homo sapiens

<400> SEQUENCE: 2

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala

```
                    85                  90                  95

Ala Asp Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
                115                 120                 125

Val Pro Glu Leu Ile Arg Thr Ile Met Gly Trp Thr Leu Asp Phe Leu
            130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
                180                 185                 190

<210> SEQ ID NO 3
<211> LENGTH: 236
<212> TYPE: PRT
<213> ORGANISM: Mus musculus

<400> SEQUENCE: 3

Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Ala Asp Ala Ala Pro Leu Gly Ala Ala Pro Thr Pro Gly Ile
            35                  40                  45

Phe Ser Phe Gln Pro Glu Ser Asn Pro Met Pro Ala Val His Arg Asp
    50                  55                  60

Met Ala Ala Arg Thr Ser Pro Leu Arg Pro Leu Val Ala Thr Ala Gly
65                  70                  75                  80

Pro Ala Leu Ser Pro Val Pro Pro Val His Leu Thr Leu Arg Arg
                85                  90                  95

Ala Gly Asp Asp Phe Ser Arg Arg Tyr Arg Arg Asp Phe Ala Glu Met
                100                 105                 110

Ser Ser Gln Leu His Leu Thr Pro Phe Thr Ala Arg Gly Arg Phe Ala
                115                 120                 125

Thr Val Val Glu Glu Leu Phe Arg Asp Gly Val Asn Trp Gly Arg Ile
            130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
                180                 185                 190

Asp Ala Phe Val Glu Leu Tyr Gly Pro Ser Met Arg Pro Leu Phe Asp
                195                 200                 205

Phe Ser Trp Leu Ser Leu Lys Thr Leu Leu Ser Leu Ala Leu Val Gly
            210                 215                 220

Ala Cys Ile Thr Leu Gly Ala Tyr Leu Gly His Lys
225                 230                 235

<210> SEQ ID NO 4
<211> LENGTH: 192
<212> TYPE: PRT
<213> ORGANISM: Mus musculus
```

<400> SEQUENCE: 4

Met Asp Gly Ser Gly Glu Gln Leu Gly Ser Gly Pro Thr Ser Ser
1               5                   10                  15

Glu Gln Ile Met Lys Thr Gly Ala Phe Leu Leu Gln Gly Phe Ile Gln
            20                  25                  30

Asp Arg Ala Gly Arg Met Ala Gly Glu Thr Pro Glu Leu Thr Leu Glu
        35                  40                  45

Gln Pro Pro Gln Asp Ala Ser Thr Lys Lys Leu Ser Glu Cys Leu Arg
    50                  55                  60

Arg Ile Gly Asp Glu Leu Asp Ser Asn Met Glu Leu Gln Arg Met Ile
65                  70                  75                  80

Ala Asp Val Asp Thr Asp Ser Pro Arg Glu Val Phe Phe Arg Val Ala
                85                  90                  95

Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Val Trp Ile Gln Asp Gln Gly Gly Trp Glu Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 5
<211> LENGTH: 205
<212> TYPE: PRT
<213> ORGANISM: Homo sapiens

<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205

<210> SEQ ID NO 6
<211> LENGTH: 233
<212> TYPE: PRT
<213> ORGANISM: Homo sapiens

<400> SEQUENCE: 6

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 7
<211> LENGTH: 193
<212> TYPE: PRT
<213> ORGANISM: Homo sapiens

<400> SEQUENCE: 7

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

```
Ala Ala Gln Leu His Val Thr Pro Gly Ser Ala Gln Gln Arg Phe Thr
 65                  70                  75                  80

Gln Val Ser Asp Glu Leu Phe Gln Gly Gly Pro Asn Trp Gly Arg Leu
                 85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 8
<211> LENGTH: 350
<212> TYPE: PRT
<213> ORGANISM: Homo sapiens

<400> SEQUENCE: 8

Met Phe Gly Leu Lys Arg Asn Ala Val Ile Gly Leu Asn Leu Tyr Cys
  1               5                  10                  15

Gly Gly Ala Gly Leu Ala Gly Ser Gly Gly Ala Thr Arg Pro Gly Gly
             20                  25                  30

Gly Arg Leu Leu Ala Thr Glu Lys Glu Ala Ser Ala Arg Arg Glu Ile
         35                  40                  45

Gly Gly Gly Glu Ala Gly Ala Val Ile Gly Ser Ala Gly Ala Ser
     50                  55                  60

Pro Pro Ser Thr Leu Thr Pro Asp Ser Arg Arg Val Ala Arg Pro Pro
 65                  70                  75                  80

Pro Ile Gly Ala Glu Val Pro Asp Val Thr Ala Thr Pro Ala Arg Leu
                 85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Asp Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240
```

```
Asp Asp Val Lys Ser Leu Ser Arg Val Met Ile His Val Phe Ser Asp
            245                 250                 255

Gly Val Thr Asn Trp Gly Arg Ile Val Thr Leu Ile Ser Phe Gly Ala
        260                 265                 270

Phe Val Ala Lys His Leu Lys Thr Ile Asn Gln Glu Ser Cys Ile Glu
    275                 280                 285

Pro Leu Ala Glu Ser Ile Thr Asp Val Leu Val Arg Thr Lys Arg Asp
290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 9
<211> LENGTH: 175
<212> TYPE: PRT
<213> ORGANISM: Homo sapiens

<400> SEQUENCE: 9

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
            20                  25                  30

Thr Ser Arg Val Leu Gln Asn Val Ala Phe Ser Val Gln Lys Glu Val
        35                  40                  45

Glu Lys Asn Leu Lys Ser Cys Leu Asp Asn Val Asn Val Ser Val
    50                  55                  60

Asp Thr Ala Arg Thr Leu Phe Asn Gln Val Met Glu Lys Glu Phe Glu
65                  70                  75                  80

Asp Gly Ile Ile Asn Trp Gly Arg Ile Val Thr Ile Phe Ala Phe Glu
                85                  90                  95

Gly Ile Leu Ile Lys Lys Leu Leu Arg Gln Gln Ile Ala Pro Asp Val
            100                 105                 110

Asp Thr Tyr Lys Glu Ile Ser Tyr Phe Val Ala Glu Phe Ile Met Asn
        115                 120                 125

Asn Thr Gly Glu Trp Ile Arg Gln Asn Gly Gly Trp Glu Asn Gly Phe
    130                 135                 140

Val Lys Lys Phe Glu Pro Lys Ser Gly Trp Met Thr Phe Leu Glu Val
145                 150                 155                 160

Thr Gly Lys Ile Cys Glu Met Leu Ser Leu Leu Lys Gln Tyr Cys
                165                 170                 175

<210> SEQ ID NO 10
<211> LENGTH: 163
<212> TYPE: PRT
<213> ORGANISM: Homo sapiens

<400> SEQUENCE: 10

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
            20                  25                  30

Thr Ser Arg Val Leu Gln Asn Val Ala Phe Ser Val Gln Lys Glu Val
        35                  40                  45
```

-continued

Glu Lys Asn Leu Lys Ser Cys Leu Asp Asn Val Asn Val Ser Val
 50                  55                  60

Asp Thr Ala Arg Thr Leu Phe Asn Gln Val Met Glu Lys Glu Phe Glu
 65                  70                  75                  80

Asp Gly Ile Ile Asn Trp Gly Arg Ile Val Thr Ile Phe Ala Phe Glu
                 85                  90                  95

Gly Ile Leu Ile Lys Lys Leu Leu Arg Gln Gln Ile Ala Pro Asp Val
            100                 105                 110

Asp Thr Tyr Lys Glu Ile Ser Tyr Phe Val Ala Glu Phe Ile Met Asn
        115                 120                 125

Asn Thr Gly Glu Trp Ile Arg Gln Asn Gly Gly Trp Gly Lys Trp His
130                 135                 140

Asn His Thr Pro Met Leu Val Glu Ser Val Ala His Lys Lys Arg Lys
145                 150                 155                 160

Met Ala Leu

<210> SEQ ID NO 11
<211> LENGTH: 194
<212> TYPE: PRT
<213> ORGANISM: Homo sapiens

<400> SEQUENCE: 11

Met Ala Asp Pro Leu Arg Glu Arg Thr Glu Leu Leu Leu Ala Asp Tyr
1               5                   10                  15

Leu Gly Tyr Cys Ala Arg Glu Pro Gly Thr Pro Glu Pro Ala Pro Ser
            20                  25                  30

Thr Pro Glu Ala Ala Val Leu Arg Ser Ala Ala Ala Arg Leu Arg Gln
        35                  40                  45

Ile His Arg Ser Phe Phe Ser Ala Tyr Leu Gly Tyr Pro Gly Asn Arg
    50                  55                  60

Phe Glu Leu Val Ala Leu Met Ala Asp Ser Val Leu Ser Asp Ser Pro
65                  70                  75                  80

Gly Pro Thr Trp Gly Arg Val Val Thr Leu Val Thr Phe Ala Gly Thr
                85                  90                  95

Leu Leu Glu Arg Gly Pro Leu Val Thr Ala Arg Trp Lys Lys Trp Gly
            100                 105                 110

Phe Gln Pro Arg Leu Lys Glu Gln Glu Gly Asp Val Ala Arg Asp Cys
        115                 120                 125

Gln Arg Leu Val Ala Leu Leu Ser Ser Arg Leu Met Gly Gln His Arg
    130                 135                 140

Ala Trp Leu Gln Ala Gln Gly Gly Trp Asp Gly Phe Cys His Phe Phe
145                 150                 155                 160

Arg Thr Pro Phe Pro Leu Ala Phe Trp Arg Lys Gln Leu Val Gln Ala
                165                 170                 175

Phe Leu Ser Cys Leu Leu Thr Thr Ala Phe Ile Tyr Leu Trp Thr Arg
            180                 185                 190

Leu Leu

<210> SEQ ID NO 12
<211> LENGTH: 233
<212> TYPE: PRT
<213> ORGANISM: Homo sapiens

<400> SEQUENCE: 12

Met Ser Gln Ser Asn Arg Glu Leu Val Val Asp Phe Leu Ser Tyr Lys
1               5                   10                  15

```
Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
 50                  55                  60

Val Asn Gly Ala Thr Gly His Ser Ser Leu Asp Ala Arg Glu Val
 65              70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
           100                 105                 110

His Ile Thr Pro Gly Thr Ala Tyr Gln Ser Phe Glu Gln Val Val Asn
           115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
           180                 185                 190

Glu Leu Tyr Gly Asn Asn Ala Ala Ala Glu Ser Arg Lys Gly Gln Glu
           195                 200                 205

Arg Phe Asn Arg Trp Phe Leu Thr Gly Met Thr Val Ala Gly Val Val
           210                 215                 220

Leu Leu Gly Ser Leu Phe Ser Arg Lys
225                 230

<210> SEQ ID NO 13
<211> LENGTH: 204
<212> TYPE: PRT
<213> ORGANISM: Homo sapiens

<400> SEQUENCE: 13

Met Val Asp Gln Leu Arg Glu Arg Thr Thr Met Ala Asp Pro Leu Arg
 1               5                  10                  15

Glu Arg Thr Glu Leu Leu Leu Ala Asp Tyr Leu Gly Tyr Cys Ala Arg
            20                  25                  30

Glu Pro Gly Thr Pro Glu Pro Ala Pro Ser Thr Pro Glu Ala Ala Val
        35                  40                  45

Leu Arg Ser Ala Ala Ala Arg Leu Arg Gln Ile His Arg Ser Phe Phe
 50                  55                  60

Ser Ala Tyr Leu Gly Tyr Pro Gly Asn Arg Phe Glu Leu Val Ala Leu
 65              70                  75                  80

Met Ala Asp Ser Val Leu Ser Asp Ser Pro Gly Pro Thr Trp Gly Arg
                85                  90                  95

Val Val Thr Leu Val Thr Phe Ala Gly Thr Leu Leu Glu Arg Gly Pro
           100                 105                 110

Leu Val Thr Ala Arg Trp Lys Lys Trp Gly Phe Gln Pro Arg Leu Lys
           115                 120                 125

Glu Gln Glu Gly Asp Val Ala Arg Asp Cys Gln Arg Leu Val Ala Leu
130                 135                 140

Leu Ser Ser Arg Leu Met Gly Gln His Arg Ala Trp Leu Gln Ala Gln
```

```
            145                 150                 155                 160
Gly Gly Trp Asp Gly Phe Cys His Phe Phe Arg Thr Pro Phe Pro Leu
                165                 170                 175
Ala Phe Trp Arg Lys Gln Leu Val Gln Ala Phe Leu Ser Cys Leu Leu
                180                 185                 190
Thr Thr Ala Phe Ile Tyr Leu Trp Thr Arg Leu Leu
                195                 200

<210> SEQ ID NO 14
<211> LENGTH: 350
<212> TYPE: PRT
<213> ORGANISM: Homo sapiens

<400> SEQUENCE: 14

Met Phe Gly Leu Lys Arg Asn Ala Val Ile Gly Leu Asn Leu Tyr Cys
1               5                   10                  15
Gly Gly Ala Gly Leu Gly Ala Gly Ser Gly Gly Ala Thr Arg Pro Gly
                20                  25                  30
Gly Arg Leu Leu Ala Thr Glu Lys Glu Ala Ser Ala Arg Glu Ile
                35                  40                  45
Gly Gly Gly Glu Ala Gly Ala Val Ile Gly Gly Ser Ala Gly Ala Ser
            50                  55                  60
Pro Pro Ser Thr Leu Thr Pro Asp Ser Arg Arg Val Ala Arg Pro Pro
65                  70                  75                  80
Pro Ile Gly Ala Glu Val Pro Asp Val Thr Ala Thr Pro Ala Arg Leu
                85                  90                  95
Leu Phe Phe Ala Pro Thr Arg Arg Ala Ala Pro Leu Glu Glu Met Glu
                100                 105                 110
Ala Pro Ala Ala Asp Ala Ile Met Ser Pro Glu Glu Glu Leu Asp Gly
                115                 120                 125
Tyr Glu Pro Glu Pro Leu Gly Lys Arg Pro Ala Val Leu Pro Leu Leu
                130                 135                 140
Glu Leu Val Gly Glu Ser Gly Asn Asn Thr Ser Thr Asp Gly Ser Leu
145                 150                 155                 160
Pro Ser Thr Pro Pro Ala Glu Glu Glu Asp Glu Leu Tyr Arg
                165                 170                 175
Gln Ser Leu Glu Ile Ile Ser Arg Tyr Leu Arg Glu Gln Ala Thr Gly
                180                 185                 190
Ala Lys Asp Thr Lys Pro Met Gly Arg Ser Gly Ala Thr Ser Arg Lys
                195                 200                 205
Ala Leu Glu Thr Leu Arg Arg Val Gly Asp Gly Val Gln Arg Asn His
                210                 215                 220
Glu Thr Ala Phe Gln Gly Met Leu Arg Lys Leu Asp Ile Lys Asn Glu
225                 230                 235                 240
Asp Asp Val Lys Ser Leu Ser Arg Val Met Ile His Val Phe Ser Asp
                245                 250                 255
Gly Val Thr Asn Trp Gly Arg Ile Val Thr Leu Ile Ser Phe Gly Ala
                260                 265                 270
Phe Val Ala Lys His Leu Lys Thr Ile Asn Gln Glu Ser Cys Ile Glu
                275                 280                 285
Pro Leu Ala Glu Ser Ile Thr Asp Val Leu Val Arg Thr Lys Arg Asp
                290                 295                 300
Trp Leu Val Lys Gln Arg Gly Trp Asp Gly Phe Val Glu Phe Phe His
305                 310                 315                 320
```

```
Val Glu Asp Leu Glu Gly Gly Ile Arg Asn Val Leu Ala Phe Ala
            325                 330                 335

Gly Val Ala Gly Val Gly Ala Gly Leu Ala Tyr Leu Ile Arg
            340                 345                 350

<210> SEQ ID NO 15
<211> LENGTH: 227
<212> TYPE: PRT
<213> ORGANISM: Homo sapiens

<400> SEQUENCE: 15

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Val Arg Thr Lys
            180                 185                 190

Pro Leu Val Cys Pro Phe Ser Leu Ala Ser Gly Gln Arg Ser Pro Thr
        195                 200                 205

Ala Leu Leu Leu Tyr Leu Phe Leu Leu Cys Trp Val Ile Val Gly Asp
    210                 215                 220

Val Asp Ser
225

<210> SEQ ID NO 16
<211> LENGTH: 427
<212> TYPE: PRT
<213> ORGANISM: Homo sapiens

<400> SEQUENCE: 16

Met Glu Ala Met Ala Ala Ser Thr Ser Leu Pro Asp Pro Gly Asp Phe
1               5                   10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
    50                  55                  60
```

-continued

```
Asp Cys Arg Ile Thr Lys Asp Asn Arg Arg His Cys Gln Ala Cys Arg
 65                  70                  75                  80

Leu Lys Arg Cys Val Asp Ile Gly Met Met Lys Glu Phe Ile Leu Thr
                 85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Val Arg Val Asn
145                 150                 155                 160

Asp Gly Gly Ser His Pro Ser Arg Pro Asn Ser Arg His Thr Pro
                165                 170                 175

Ser Phe Ser Gly Asp Ser Ser Ser Cys Ser Asp His Cys Ile Thr
                180                 185                 190

Ser Ser Asp Met Met Asp Ser Ser Phe Ser Asn Leu Asp Leu Ser
            195                 200                 205

Glu Glu Asp Ser Asp Asp Pro Ser Val Thr Leu Glu Leu Ser Gln Leu
        210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
    290                 295                 300

His Ser Leu Glu Leu Ile Glu Pro Leu Ile Lys Phe Gln Val Gly Leu
305                 310                 315                 320

Lys Lys Leu Asn Leu His Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Pro Gly Ser His Leu Leu Tyr Ala Lys Met Ile
    370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425

<210> SEQ ID NO 17
<211> LENGTH: 422
<212> TYPE: PRT
<213> ORGANISM: Mus musculus

<400> SEQUENCE: 17

Met Glu Ala Met Ala Ala Ser Thr Ser Leu Pro Asp Pro Gly Asp Phe
 1                   5                  10                  15
```

-continued

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
            35                  40                  45

Arg Arg Ser Met Lys Arg Lys Ala Leu Phe Thr Cys Pro Phe Asn Gly
50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Val Gln Arg Lys Arg Glu Met Ile Met Lys Arg Lys Glu
            100                 105                 110

Glu Glu Ala Leu Lys Asp Ser Leu Arg Pro Lys Leu Ser Glu Glu Gln
            115                 120                 125

Gln His Ile Ile Ala Ile Leu Leu Asp Ala His His Lys Thr Tyr Asp
130                 135                 140

Pro Thr Tyr Ala Asp Phe Arg Asp Phe Arg Pro Pro Ile Arg Ala Asp
145                 150                 155                 160

Val Ser Thr Gly Ser Tyr Ser Pro Arg Pro Thr Leu Ser Phe Ser Gly
                165                 170                 175

Asp Ser Ser Ser Asn Ser Asp Leu Tyr Thr Pro Ser Leu Asp Met Met
            180                 185                 190

Glu Pro Ala Ser Phe Ser Thr Met Asp Leu Asn Glu Glu Gly Ser Asp
        195                 200                 205

Asp Pro Ser Val Thr Leu Asp Leu Ser Pro Leu Ser Met Leu Pro His
    210                 215                 220

Leu Ala Asp Leu Val Ser Tyr Ser Ile Gln Lys Val Ile Gly Phe Ala
225                 230                 235                 240

Lys Met Ile Pro Gly Phe Arg Asp Leu Thr Ser Asp Asp Gln Ile Val
                245                 250                 255

Leu Leu Lys Ser Ser Ala Ile Glu Val Ile Met Leu Arg Ser Asn Gln
            260                 265                 270

Ser Phe Thr Leu Asp Asp Met Ser Trp Asp Cys Gly Ser Gln Asp Tyr
        275                 280                 285

Lys Tyr Asp Ile Thr Asp Val Ser Arg Ala Gly His Thr Leu Glu Leu
    290                 295                 300

Ile Glu Pro Leu Ile Lys Phe Gln Val Gly Leu Lys Lys Leu Asn Leu
305                 310                 315                 320

His Glu Glu Glu His Val Leu Leu Met Ala Ile Cys Ile Val Ser Pro
                325                 330                 335

Asp Arg Pro Gly Val Gln Asp Ala Lys Leu Val Glu Ala Ile Gln Asp
            340                 345                 350

Arg Leu Ser Asn Thr Leu Gln Thr Tyr Ile Arg Cys Arg His Pro Pro
        355                 360                 365

Pro Gly Ser His Gln Leu Tyr Ala Lys Met Ile Gln Lys Leu Ala Asp
    370                 375                 380

Leu Arg Ser Leu Asn Glu Glu His Ser Lys Gln Tyr Arg Ser Leu Ser
385                 390                 395                 400

Phe Gln Pro Glu Asn Ser Met Lys Leu Thr Pro Leu Val Leu Glu Val
                405                 410                 415

Phe Gly Asn Glu Ile Ser
            420

```
<210> SEQ ID NO 18
<211> LENGTH: 35
<212> TYPE: DNA
<213> ORGANISM: Artificial Sequence
<220> FEATURE:
<223> OTHER INFORMATION: Oligonucleotide for directed mutagenesis

<400> SEQUENCE: 18
ggctgccagg acggctcctc tcaggcccct cgttg                         35

<210> SEQ ID NO 19
<211> LENGTH: 44
<212> TYPE: DNA
<213> ORGANISM: Artificial Sequence
<220> FEATURE:
<223> OTHER INFORMATION: Oligonucleotide for directed mutagenesis

<400> SEQUENCE: 19
gggacatggc tgccagggag gagcctctca ggcccctcgt tgcc               44

<210> SEQ ID NO 20
<211> LENGTH: 35
<212> TYPE: DNA
<213> ORGANISM: Artificial Sequence
<220> FEATURE:
<223> OTHER INFORMATION: Oligonucleotide for directed mutagenesis

<400> SEQUENCE: 20
caacgagggg cctgagagga gccgtcctgg cagcc                         35

<210> SEQ ID NO 21
<211> LENGTH: 44
<212> TYPE: DNA
<213> ORGANISM: Artificial Sequence
<220> FEATURE:
<223> OTHER INFORMATION: Oligonucleotide for directed mutagenesis

<400> SEQUENCE: 21
ggcaacgagg ggcctgagag gctcctccct ggcagccatg tccc               44
```

TRANS-DIFFERENTIATION OF DIFFERENTIATION CELLS

RELATED APPLICATIONS

This application is a § 371 national-stage application based on PCT Application WO 2015/114059, filed Jan. 29, 2015, which claims the benefit of priority to EP 14153104, filed Jan. 29, 2014.

SEQUENCE LISTING

This application contains a sequence listing in the form of an ASCII text file, named SWH-00501-SeqList-v2.txt, the last version of which was created on Nov. 15, 2018, and which has a size of 38,454 bytes. The sequence listing is hereby incorporated by reference herein in its entirety.

The present invention relates to a method of trans-differentiating differentiated cells, the method comprising bringing said cells into contact with at least one component (i) and at least one component (ii), wherein said component (i) is selected from (a) a polypeptide comprising at least one domain selected from the group consisting of a BH1, a BH2, a BH3 and a BH4 domain; (b) a polypeptide comprising or consisting of the amino acid sequence of a wild-type form of a member of the Bcl-2 family or a fragment thereof; (c) a polypeptide comprising or consisting of the amino acid sequence of a wild-type form of a member of the Bcl-2 family or a fragment thereof, wherein said polypeptide comprises one or more point mutations as compared to said wild-type form or fragment thereof; (d) a polypeptide comprising or consisting of an amino acid sequence which sequence exhibits at least 30% sequence identity with a wild-type form of a member of the Bcl-2 family, said wild-type form of a member of the Bcl-2 family preferably being selected from the group consisting of human Bcl-2 (SEQ ID NO: 1 or 5), human Bcl-$X_L$ (SEQ ID NO: 6), human Bcl-w (SEQ ID NO: 7), human Mcl1 (SEQ ID NO: 8), human Bfl1 (SEQ ID NO: 9 or 10), human Nrh (SEQ ID NO: 11), human Bcl2L1 (SEQ ID NO: 12), human DIVA (SEQ ID NO: 13), human myeloid cell leukemia sequence 1 isoform 1 (SEQ ID NO: 14), and human Bcl-x beta (SEQ ID NO: 15); wherein said wild-type form has anti-apoptotic activity; a nucleic acid encoding said polypeptide; and means for enhancing the amount and/or activity of said polypeptide in said cells; wherein said component (i) enhances the yield of trans-differentiated cells by at least 30% as compared to the absence of said component (i); and wherein said component (ii) is selected from a transcription factor capable of trans-differentiating said cells; a nucleic acid encoding said transcription factor; and means for enhancing the amount and/or activity of said transcription factor in said cells; wherein any method of treatment of the human or animal body by therapy is excluded.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Stem cell research has spawned various approaches to cell and tissue regeneration. Stem cells as such, owing to their pluripotency, are a preferred starting material for regeneration. However, their availability, in particular from an autologous source, is generally limited. More recent approaches see the use of differentiated cells as starting material moving into focus. The process referred to as dedifferentiation involves the restoration of pluripotency in a fully differentiated cell. Once a pluripotent state has been reached, the obtained induced pluripotent cells in turn may be used as starting material for a subsequent step of induced differentiation to the desired cell type. A hallmark of this approach is that the cells go through a pluripotent state. Yet more recent, and generally unsatisfactory in terms of performance and yield, trans-differentiation has been described. This term in essence designates a process of converting a differentiated cell into another differentiated cell, wherein during the process of trans-differentiation the cells do not go through a pluripotent state. A recent review which also deals with terminology is Jopling et al. (Nature Reviews, Molecular Cell Biology, 11, 79-89 (2011)).

Direct trans-differentiation of somatic cells into different lineages allows generation of specific cell types which can otherwise not easily be harnessed. This is in particular the case for postmitotic cells that cannot be amplified in vitro and whose isolation and expansion from adult humans is thus not possible, such as neurons. Direct trans-differentiation of different cell types into fully functional neurons (see e.g. Berninger et al., Journal of Neuroscience, 27, 8654-8664, (2007); Heinrich et al., PLoS biology, 8, e1000373 (2010); Vierbuchen et al., Nature, 463, 1035-1041 (2011)) is thus a useful approach to examine neurons from various species and cell sources. However, efficiency of generation and purity of such induced neurons (iNs) is not satisfactory, and basic principles aiding this direct reprogramming remain to be unraveled. We note that trans-differentiation is sometimes also referred to as "direct reprogramming".

Certain neurogenic transcription factors are known, however, basic principles of how they work still remain to be elucidated. For example, direct down-stream effectors activated in the context of trans-differentiation are still not known. Accordingly, it is also not clear to which extent different transcription factors are required in cells from different organs for the generation of iNs or whether there are 'neuronal master genes' whose expression in various cell types promotes the generation of neurons. On the one hand, rather different factors have been shown to work in different cell types, such as Neurog2 that trans-differentiates astrocytes into neurons, but seems to be less efficient in fibroblasts (Heinrich et al. (loc. cit.); Vierbuchen et al. (loc. cit.)) or Myt1I that is efficient in fibroblasts but not in astrocytes. Conversely, other transcription factors, such as Ascl1 and/or Sox2, proved to be useful for generating neurons from various cell sources, such as astrocytes (Berninger et al. (loc. cit.); Heinrich et al. (loc. cit.)), fibroblasts (Vierbuchen et al. (loc. cit.)) and pericytes (Karow et al, Cell stem cell, 11, 471-476 (2012)). Moreover, efficiency of neurogenic transcription factors often appears to be rather different in cells derived from different species, such as mouse and human (see e.g. Vierbuchen et al. (loc. cit.)). Often the same neurogenic transcription factors require distinct combinations of additional neurogenic transcription factors, such as NeuroD or Sox11 or Myt1I, depending on the cellular and species context. It therefore still remains elusive to which extent common or different mechanisms are at work in these different starting cells.

Bcl-2, an anti-apoptotic member of the Bcl-2 family has been implicated in the process of dedifferentiation. Generally, its anti-apoptotic property is viewed as being responsible for enhanced survival in processes involving a change of cell fate. For example, Kawamura et al. (Nature 460, 1140-1144 (2009)) describe the reprogramming of somatic cells to induce pluripotent stem cells. The authors observed that the overexpression of Bcl-2 suppressed apoptosis and increased the frequency of Nanog-expressing cells, Nanog being a pluripotency marker. Liu et al. (Stem Cells, 29, 2077-2089 (2011)) found Bcl-2 to be overexpressed in dedifferentiated mesenchymal stem cells. Also in this publication, the anti-apoptotic properties of Bcl-2 are considered relevant. A further hallmark of the prior art in that field is more than one transcription factor, sometimes complex mixtures of transcription factors are used to achieve a change in cell fate.

The involvement and possible role of Bcl-2 in neuronal regeneration is less clear and is controversially discussed. For example, Bernier and Parent (The Journal of Neuroscience, 18, 2486-2497 (1998)) describe Bcl-2 as a marker of neuronal immaturity and furthermore note that this protein would have been shown to promote regeneration of severed axons. Quite to the contrary, Inoue et al. (The Journal of Neuroscience, 22, 4468-4477 (2002)) reported that Bcl-2 overexpression does not enhance in vivo axonal regeneration.

In view of the prior art, the technical problem underlying the present invention can be seen in the provision of alternative or improved means and methods for trans-differentiating differentiated cells. This problem has been solved by the enclosed claims.

Accordingly, in a first aspect, the present invention relates to a method of trans-differentiating differentiated cells, the method comprising bringing said cells into contact with at least one component (i) and at least one component (ii), wherein said component (i) is selected from (a) a polypeptide comprising at least one domain selected from the group consisting of a BH1, a BH2, a BH3 and a BH4 domain; (b) a polypeptide comprising or consisting of the amino acid sequence of a wild-type form of a member of the Bcl-2 family or a fragment thereof; (c) a polypeptide comprising or consisting of the amino acid sequence of a wild-type form of a member of the Bcl-2 family or a fragment thereof, wherein said polypeptide comprises one or more point mutations as compared to said wild-type form or fragment thereof; (d) a polypeptide comprising or consisting of an amino acid sequence which sequence exhibits at least 30% sequence identity with a wild-type form of a member of the Bcl-2 family, said wild-type form of a member of the Bcl-2 family preferably being selected from the group consisting of human Bcl-2 (SEQ ID NO: 1 or 5), human Bcl-$X_L$ (SEQ ID NO: 6), human Bcl-w (SEQ ID NO: 7), human Mcl1 (SEQ ID NO: 8), human Bfl1 (SEQ ID NO: 9 or 10), human Nrh (SEQ ID NO: 11), human Bcl2L1 (SEQ ID NO: 12), human DIVA (SEQ ID NO: 13), human myeloid cell leukemia sequence 1 isoform 1 (SEQ ID NO: 14), and human Bcl-x beta (SEQ ID NO: 15); wherein said wild-type form has anti-apoptotic activity; a nucleic acid encoding said polypeptide; and means for enhancing the amount and/or activity of said polypeptide in said cells; wherein said component (i) enhances the yield of trans-differentiated cells by at least 30% as compared to the absence of said component (i); and wherein said component (ii) is selected from a transcription factor capable of trans-differentiating said cells; a nucleic acid encoding said transcription factor; and means for enhancing the amount and/or activity of said transcription factor in said cells; wherein any method of treatment of the human or animal body by therapy is excluded.

Related thereto, the present invention provides a method of trans-differentiating differentiated cells, the method comprising bringing said cells into contact with (i) a polypeptide comprising at least one domain selected from the group consisting of a BH1, a BH2, a BH3 and a BH4 domain, a nucleic acid encoding said polypeptide, and/or means for enhancing the amount or activity of said polypeptide in said cells, which polypeptide, nucleic acid encoding said polypeptide, or means for enhancing the amount or activity of said polypeptide in said cells enhances the yield of trans-differentiated cells by at least 50% as compared to the absence of said polypeptide, nucleic acid encoding said polypeptide, or means for enhancing the amount or activity of said polypeptide in said cells, respectively; and (ii) one or more transcription factors capable of trans-differentiating said cells; one or more nucleic acids encoding said one or more transcription factors; and/or means for enhancing the amount of said one or more transcription factors in said cells, wherein any method of treatment of the human or animal body by therapy is excluded.

The term "trans-differentiating" has its art-established meaning. In particular, it refers to converting one type of differentiated cell into a second, distinct type of differentiated cell. Different from dedifferentiation followed by differentiation, trans-differentiation does not involve an intermediate state which is pluripotent in nature. Trans-differentiation in accordance with the present invention may be performed with dividing or non-dividing cells. Furthermore, it may be performed with proliferating and non-proliferating cells.

The avoidance of a pluripotent state has distinct advantages. For example, pluripotent cells are generally perceived as being potentially tumorigenic. Therefore, the avoidance of a pluripotent state confers a higher degree of safety as compared to alternative routes of preparing differentiated cells, which alternative routes proceed via a pluripotent state. Additionally, direct trans-differentiation avoids a first step of de-differentiating and therefore reduces the time required to obtain the desired cell type.

The term "differentiated cell" has its art-established meaning. Differentiated cells are specialized cells. Examples of such specialized cell types are muscle cells and nerve cells. In a number of instances, differentiated cells are confined to certain tissues of the mature organism. Under normal circumstances, differentiated cells are not capable of either dedifferentiation or other changes of cell fate. As shown in the examples, the method of the present invention works independent of the starting cell type (herein above also referred to as "differentiated cell"). In particular, there is no limitation to differentiated cells of ectodermal origin. Rather, the method works efficiently for differentiated cells derived from different germ layers. Also, it works with cells originating from different species. All this is evidenced by the examples enclosed herewith.

Without wishing to be bound by a particular theory, it is considered that the process of trans-differentiating involves changes in the gene expression pattern of the target differentiated cells (the starting cell type). Therefore, it is understood that components (i) and (ii) of the first aspect of the invention preferably have to cross the cell membrane of the targeted differentiated cell in order to exert their effect. In other words, said bringing into contact is preferably to be effected under conditions which permit such crossing of the cell membrane. The skilled person is aware of appropriate methods. Without wishing to be bound by a specific theory, it is furthermore considered that for transcription factors to exert their effect, they need to be present in the cell nucleus. Also with regard to the polypeptide in accordance with item (i) of the first aspect, there are indications that said polypeptide exerts its effect when it is present within the cell nucleus. Presence in the cell nucleus may either be achieved by delivery to the nucleus or by transport mechanism present within the targeted differentiated cell such that the crossing of the cell membrane will generally be sufficient for achieving trans-differentiation.

To the extent the agents in accordance with items (i) and (ii) of the first aspect are nucleic acids, transduction and transfection are preferred means of bringing cells into contact with said agents. Various chemicals have been described for the purpose of aiding in the delivery of nucleic acids to cells, such chemicals including calcium phosphate, amphiphatic molecules capable of forming liposomes, and cationic polymers such as polyethyleneimine. Commonly used transfection reagents and kits, in particular for transfecting primary fibroblasts are NucleofactorT Kit (Lonza) and FuGENE® 6 Transfection Reagent (Promega, Roche Applied Science). Physical methods include electroporation and the use of a gene gun. In a further alternative, viruses may be used as vectors.

Physical and chemical methods have also been adapted for delivery of peptide, polypeptides or proteins to cells. In many instances, the fraction of protein crossing the cell membrane can be enhanced by fusing short peptides to the polypeptide to be delivered. These short peptides are known in the art as cell penetrating peptides (CPP) or protein transduction domains (PTD).

While delivery of polypeptides or nucleic acids encoding said polypeptides is preferred, delivery of nucleic acids being particularly preferred, further options are envisaged for the purpose of practicing the present invention. In this regard, it is understood that wild-type forms of the polypeptide in accordance with the first aspect are encoded by the genomic DNA present in the differentiated cell to be trans-differentiated. Similarly, also wild-type forms of said transcription factors in accordance with the first aspect are encoded by the endogenous DNA of said differentiated cells. To the extent use shall be made of said endogenous factors, any means capable of enhancing the amount and/or activity of the corresponding translation product, i.e. said polypeptide or said transcription factor, are suitable for practicing the present invention. To give an example, a transcription factor enhancing the expression of said polypeptide, e.g. of human Bcl-2 is a suitable means. A further means for enhancing the expression and/or activity of said polypeptide is forskolin, herein also designated "Fk". The above considerations apply mutatis mutandis also to those components (i) and (ii) which are not endogenously encoded by the cells. Also in that case, instead of or in addition to providing nucleic acids or polypeptides, means for enhancing the expression and/or activity may be provided. Also in the latter case, forskolin is a preferred means.

The term "polypeptide" is known in the art and refers to a polycondensate of amino acids. The minimal number of amino acids in said polypeptide is implied by any of the requirements in accordance with the definition of said polypeptide provided in the first aspect. For the sake of completeness, it is noted that said polypeptide contains at least ten amino acids. In terms of building blocks, preference is given to the 20 proteinogenic amino acids. The amino acids may be modified, for example by glycosylation, acetylation, phosphorylation and further modifications which are well known in the art. The termini may be protected, e.g., the amino terminus may acetylated and/or the carboxy terminus may amidated. In addition to the 20 proteinogenic amino acids, other amino acids may constitute up to 10%, up to 20%, up to 30%, up to 40% or up to 50% of the building blocks. Such other amino acids include the α-amino acids selenocysteine, pyrrolysin, hydroxyproline and selenomethionine, but also, in a less preferred embodiment, β-amino acids. In terms of linkage between the building blocks, preference is given to the peptide bond between the carboxyl group of a given amino acid and the amino group of the subsequent amino acid. Having said that, the presence of up to 10%, up to 20%, up to 30%, up to 40% or up to 50% isopeptide bonds, i.e. peptide bonds involving side chain carboxylates and/or amines, is envisaged. Up to 10%, 20%, 30%, 40% or 50% of the building blocks may be α-hydroxy acids such as lactate, the consequence being that a corresponding fraction of functional groups connecting adjacent building blocks is an ester group. Depsipeptides, i.e. compounds wherein adjacent building blocks are connected by peptide or ester bonds, are to be subsumed under the term "polypeptide" to the extent the fraction of ester bonds does not exceed the above recited values. The use of peptidomimetics is also envisaged. Peptidomimetics are compounds which differ from polypeptides in that one or more amino acids, subsequences of said polypeptide, or the polypeptide in its entirety is replaced by a moiety mimicking the structure of said amino acid(s), said subsequence or said polypeptide to be replaced.

Having said that, particular preference is given to polypeptides wherein the building blocks are exclusively connected by peptide bonds and/or which are exclusively made of the 20 proteinogenic amino acids.

As established in the art, the term "nucleic acids" refers to polycondensates of nucleotides which preferably contain at least 30 nucleotides. The bases comprised in said nucleotides are preferably selected from adenine, guanine, cytosine, thymine and uracil. Art-established modifications, such as 2'-O-methyl modifications may be present. The term includes DNA, such as cDNA and genomic DNA as well as RNA. A preferred RNA is mRNA.

The phrase "selected from" indicates that one, two, three or more of the subsequently numerated items may be used. As an example, the method according to the first aspect may be produced by using, as component (i), a nucleic acid encoding said polypeptide and said means as defined in relation to component (i). Particularly preferred is the use of (only) said nucleic acid.

The polypeptide according to item (a) of the first aspect of the present invention contains at least one conserved domain, said conserved domain being selected from the group consisting of a BH1, a BH2, a BH3 and a BH4 domain. These four domains are features characterizing a specific class of proteins which is involved in regulating apoptosis. The present inventors surprisingly discovered that polypeptides comprising at least one of the mentioned domains, in addition to the mentioned involvement in apoptosis are, with significant likelihood, characterized by a further function. This further function is the enhancement of trans-differentiation of differentiated cells. Provided with (i) the teaching of the present invention which establishes a link between the presence of at least one domain selected from the group consisting of a BH1, a BH2, a BH3 and a BH4 domain with a capability of enhancing trans-differentiation of differentiated cells, (ii) the art-established definitions of the mentioned domains (for details see below), and (iii) an assay for quantifying the enhancement of trans-differentiation (for details see below), one can identify in a straightforward manner polypeptides meeting the requirements of item (i) of the first aspect and successfully work the present invention.

It is understood that also the following polypeptides are polypeptides in accordance with the present invention: polypeptides comprising a BH1 domain and no BH2, no BH3 and no BH4 domain; polypeptides comprising a BH2 domain and no BH1, BH3 and BH4 domain; polypeptides comprising a BH4 domain and no BH1, BH2 and BH3 domain. Polypeptides comprising only a BH3 domain are less preferred, in particular to the extent such polypeptides have pro-apoptotic effects. Further polypeptides in accordance with the invention are those comprising a BH1 and a BH2, but no BH3 and BH4 domain; those comprising a BH1 and a BH3 but no BH2 and no BH4 domain; those comprising a BH1 and a BH4 domain, but none of the other BH domains; polypeptides comprising a BH2 and a BH4 domain, but none of the other BH domains; polypeptides comprising a BH3 and a BH4 domain, but none of the other BH domains; polypeptides comprising a BH2 and a BH3 domain, but none of the other BH domains. Also embraced are polypeptides comprising three BH domains and no further BH domain, said three BH domains being (i) a BH1, a BH2 and a BH3 domain; a BH1, a BH2 and a BH4 domain; a BH1, a BH3 and a BH4 domain or a BH2, a BH3 and a BH4 domain. Finally, and particularly preferred are polypeptides comprising a BH1, a BH2, a BH3 and a BH4 domain. In all of these polypeptides, a transmembrane domain (such transmembrane domain being present for example in human wild-type Bcl-2) may be either present or absent, the latter option being preferred.

Items (b), (c) and (d) of the first aspects are alternative means of characterizing the polypeptide in accordance with the invention.

In its broadest form, the term "fragment" in accordance with item (b) is not particularly limited other than by the requirements in accordance with the first aspect. In preferred embodiments, the fragment consists of at least 50%, at least 60%, at least 70%, at least 80% or at least 90% of the amino acid sequence of a wild-type form of a member of the Bcl-2 family, said wild-type form having anti-apoptotic activity and preferably being selected from the Bcl-2 family members defined in accordance with item (d) of the first aspect.

Similarly, the number of point mutations in accordance with item (c) is not particularly limited other than by the requirements in accordance with the first aspect. In preferred embodiments, "more point mutations" are two, three, four, five, six, seven, eight, nine or ten point mutations.

Item (d) of the first aspect defines classes of polypeptides centered around each one of human Bcl-2, human Bcl-$X_L$, human Bcl-w, etc. The degree of sequence identity is preferably at least 40%, at least 50%, at least 60%, at least 70%, at least 80%, at least 90%, at least 95%, at least 98%, at least 99% or 100%. Methods of determining sequence identity are known in the art. Two nucleotide or amino acid sequences can be aligned electronically using suitable computer programs known in the art. Such programs comprise BLAST (Altschul et al., J. Mol. Biol. 215, 403-410 (1990)), variants thereof such as WU-BLAST (Altschul & Gish, Methods Enzymol. 266, 460-480 (1996)), FASTA (Pearson & Lipman, Proc. Natl. Acad. Sci. USA 85, 2444-2448 (1988)) or implementations of the Smith-Waterman algorithm (SSEARCH, Smith & Waterman, J. Mol. Biol. 147, 195-197 (1981)). These programs, in addition to providing a pairwise sequence alignment, also report the sequence identity level (usually in percent identity) and the probability for the occurrence of the alignment by chance (P-value). Programs such as CLUSTALW (Higgins et al., Nucleic Acids Res. 22, 4673-4680 (1994)) can be used to align more than two sequences. Preferably, default settings of the respective computer programs as published are used. A preferred alignment program is BLAST (loc. cit.).

Within the context of the present invention, it is preferred to use any mutant within any of the above defined sequence identity levels of a given reference sequence, reference sequences being human Bcl-2, human Bcl-$X_L$, human Bcl-w, etc., as a mutant "derived from" said reference sequence. In many instances, and this will be further detailed below, minor changes in a wild type sequence are sufficient to reduce or abrogate anti-apoptotic function and/or enhance trans-differentiation capability.

To the extent any of the proteins in accordance with item (d) occurs naturally as more than one splice variant, any of such splice variants is embraced by the present invention and furthermore serves as a reference for defining homologues, homologues being defined in terms of sequence identity (see below). A variant of human Bcl-2, known as Bcl-2-β-isoform is included herewith as SEQ ID NO: 5. Preference is given to that form of human Bcl-2 which has the sequence of SEQ ID NO: 1.

The sequence of human Bcl-$X_L$ is herewith included as SEQ ID NO: 6. The sequence of human Bcl-w is included as SEQ ID NO: 7. The sequence of human Mcl1 is included as SEQ ID NO: 8. The sequence of isoforms 1 and 2 of human Bfl1 are included as SEQ ID NOs: 9 and 10, respectively. The sequence of human Nrh is given in SEQ ID NO: 11. The sequence of human Bcl2L1 is given in SEQ ID NO: 12. The sequence of human DIVA is given in SEQ ID NO: 13. The sequence of human myeloid cell leukemia sequence 1 isoform 1 is given in SEQ ID NO: 14. The sequence of human Bcl-x beta is given in SEQ ID NO: 15.

Preferred is also the combination of requirements in accordance with the above item (a) and item (d).

The term "Bcl-2 family" is established in the art (Chao and Korsmeyer, Annu. Rev. Immunol. 16, 395-419 (1998)). The term "Bcl-2" designates a member of this family which, in its wild type form, has anti-apoptotic activity. "Bcl-2" is not limited with regard to the organism or species it originates from.

A suitable assay for determining the degree of enhancement of trans-differentiation is as follows. Differentiated cells, preferably human adult fibroblasts, are brought into contact with a nucleic acid encoding the neurogenic transcription factor Ascl1, wherein said bringing into contact is performed in the presence of a candidate polypeptide and in its absence. Subsequently, the quantity of trans-differentiated cells, in the present assay neurons, is counted. If the number of neurons obtained in the presence of the candidate polypeptide exceeds the number of neurons obtained in its absence by at least 30%, said candidate polypeptide is a polypeptide in accordance with the first aspect of the present invention. The assay to quantify the number of neurons is usually performed by immunocytochemistry with specific antibodies which recognizes proteins expressed exclusively in neuronal cells, such as for example β-III-tubulin, neurofilament, double-cortin or MAP-2. Preferably, β-III-tubulin immunostaining is used. For example, the cultures are fixed in 4% paraformaldehyde (PFA) in phosphate buffered saline (PBS) for 10 min at room temperature, washed in PBS and pretreated in 0.5% Triton X-100 in PBS for 30 min, followed by incubation in 2% BSA and 0.5% Triton X-100 in PBS for 30 min. Primary β-III-tubulin (mouse IgG2b, Sigma, T8660) and RFP (rabbit, 1:500, Chemicon, AB3216, or 1:2000, Rockland 600-401-379) antibodies are incubated on specimen overnight at 4° C. in 2% BSA (1:500), 0.5% Triton X-100 in PBS. After washing in PBS, cells are incubated with secondary anti-mouse and anti-rabbit antibodies conjugated to Cy™2 and Cy™3 respectively (1:500, Jackson ImmunoResearch). Then number of double positive cells (β-III-tubulin+ and RFP+) can be analysed by epifluorescence microscopy.

In preferred embodiments, the degree of enhancement of trans-differentiation is at least 40%, at least 50%, at least 60%, at least 70%, at least 80%, at least 90%, at least 100%, at least 2-fold, 3-fold, 4-fold, 5-fold, at least 10-fold, 20-fold, 50-fold or at least 100-fold.

The four above mentioned Bcl-2 homology domains are known in the art and their presence can be determined, for example, by means of pairwise sequence alignment, multiple sequence alignment or a sequence analysis using databases of conserved motifs or domains, a preferred database being Pfam (Punta et al., Nucleic acid research, database issue 40: D290-D301 (2012)). For the purpose of determining presence of the mentioned domains, it is preferred to use version 27.0 of March 2013 of the Pfam database and algorithm using default settings. For illustrative purposes we furthermore refer to Inohara et al. (The Journal of Biological Chemistry, Issue of December 4, 273, 32479-32486 (1998)) and Inohara et al. (The Journal of Biological Chemistry, Issue of April 10, 273, 8705-8710 (1998)), each displaying sequence alignments where BH1, BH2, BH3 and BH4 domains are highlighted. The residue ranges responding to a BH1 domain, BH2 domain, BH3 domain and BH4 domain (in that order) are as follows: in human Bcl-2 (sequence herewith enclosed as SEQ ID NO: 1): 136 to 155, 187 to 202, 97 to 105, and 7 to 30; in murine Bcl-2 (SEQ ID NO: 3): 133 to 151, 184 to 198, 94 to 102, and 7 to 30.

The term "polypeptide comprising at least one domain selected from the group consisting of a BH1, a BH2, a BH3 and BH4 domain" comprises both wild type forms (see above item (b)) and artificial forms, said artificial forms having no naturally occurring identical counterpart (see above item (b) to the extent it relates to fragments, items (c) and (d)). Within said artificial forms, preference is given to mutants derived from a wild type form, wherein the fact that a given mutant is derived from a wild type form is expressed in terms of sequence identity; see above item (d). To the extent use shall be made of a wild type polypeptide, said wild type form preferably has anti-apoptotic activity. The present inventors discovered that within the group of polypeptides comprising at least one domain selected from a BH1, a BH2, a BH3 and a BH4 domain, there is a subgroup with enhanced likelihood of being characterized by trans-differentiating capability, said subgroup being characterized by anti-apoptotic activity. For wild type members of the group of polypeptides defined in item (a) of the first aspect (presence of at least one of the mentioned domains), it is generally known whether they have anti-apoptotic activity. Examples of wild type polypeptides meeting the terms of the claims (presence of domains; anti-apoptotic activity) are Bcl-2, Bcl-$X_L$, Bcl-w, Mcl1, Bfl1, Nrh, Bcl2L1, DIVA, myeloid cell leukemia sequence 1 isoform 1, and Bcl-x beta. Presence, absence and degree of apoptosis may be determined, for example, by means of video time lapse tracking (see also the enclosed examples), by immunostaining for specific apoptotic events (Caspase-3 cleavage, Nicholson, D. W. et al. (1995) Nature 376, 37-43.) or using commercial kits (for example Caspase/Apoptosis Detection kit from Cell Technology, known as APO LOGIX™ Carboxyfluorescein Caspase Detection Kit).

Component (ii) of the first aspect relates to transcription factors. One or more transcription factors may be used. The term "transcription factor" has its art-established meaning. It refers to a polypeptide or protein (the term "protein" comprising polypeptides as well as compositions of matter comprising more than one polypeptide non-covalently or covalently bound to each other) which modifies the level of expression of one or more genes, said one or more genes also being referred to as target genes of the transcription factor. In order to exert its action, a transcription factor generally has to enter into the nucleus. It binds preferably to the promoter and/or an enhancer region of the one or more target genes. Said one or more transcription factors are capable of trans-differentiating said cells. Accordingly, said one or more transcription factors modify the gene expression profile of the targeted differentiated cells such that cell fate is changed. While in some instances transcription factors, or typically mixtures of more than one transcription factor are capable of triggering trans-differentiation, the yield as well as the purity of the obtained cells is generally low; see the discussion of the prior art herein above. Yet, there is established knowledge as to which transcription factors are useful for obtaining certain types of cells at the end of the trans-differentiation process. Accordingly, known transcription factors have been grouped in accordance with the type of cell which may be obtained upon their administration. Such groups include myogenic transcription factors and neurogenic transcription factors.

It is understood that the term "transcription factor" embraces both wild type transcription factors as well as functional fragments thereof. The term "functional" in relation to functional fragments of transcription factors defines those fragments which are capable of trans-differentiating cells, more preferably to achieve at least 50% of the degree of trans-differentiation which is achievable when using the corresponding wild type transcription factor. In order to determine whether a fragment of a transcription factor is a functional fragment in accordance with the present invention, the following assay may be performed. Differentiated cells, preferably adult fibroblast cells, may be brought into contact with a given transcription factor in a first assay, and with a fragment thereof in a second assay. Subsequent to that bringing into contact, the number of trans-differentiated cells is determined. For example, if said transcription factor is Neurog2, the cells obtained by said trans-differentiation process would be neurons. In case the second assay delivers at least 50% of the amount of neurons obtained in the first assay, said fragment of said transcription factor would be a functional fragment in accordance with the present invention.

Analogous to component (i), it is preferred to use one or more nucleic acids encoding one or more transcription factors. As a further alternative, means may used which enhance the amount and/or activity of said one or more transcription factors in said cells.

The present method works independently of the transcription factor. This is demonstrated in the examples. Moreover, while prior art methods routinely use mixtures of transcription factors, the method of the present invention, at least in part owing to the trans-differentiation enhancement conferred by said polypeptide, works efficiently also in presence of only one transcription factor. The term "one transcription factor" refers to one type of transcription factor, said type being defined in terms of a specific amino acid sequence. To the extent the invention is practiced with one transcription factor, it is understood that other transcription factors are absent. The term "one transcription factor" does not mean, at least not necessarily, a single molecule.

As evidenced by the examples enclosed herewith, the method according to the present invention is characterized by outstandingly high rates of trans-differentiation (up to 100%). Not only efficiency is high, but also the degree of purity of differentiated cells obtained upon trans-differentiation. The high degree of purity, without being bound by a specific theory, can be attributed to at least two features. First, the avoidance of a pluripotent state or pluripotent starting material. Secondly, and this is subject of preferred embodiments detailed below, the method of the present invention performs outstandingly also in those implementations where only one transcription factor is used. The use of only one transcription factor is a further means of ensuring purity of the obtained cells.

The present inventors furthermore discovered that the checkpoint for trans-differentiation is dependent on oxidative stress. Preferably, said oxidative stress is peroxidation of lipids. An example for determination of lipid peroxidation can be found in the method described by Drummen and collaborators (Drummen et al., 2002). The term "checkpoint" has its art-established meaning. In particular, it refers to a cellular mechanism which decides upon cell fate. In the context of trans-differentiation, a checkpoint decides upon whether the cells proceed on the path of trans-differentiation or whether they undergo different fates, said different fates typically being apoptosis or ferroptosis. Ferroptosis is an ion-dependent form of non-apoptotic cell death (Dixon and Stockwell, 2014). Oxidative stress, in particular lipid peroxidation, has an inhibitory effect on trans-differentiation and we observed that the component (i) reduces lipid peroxidadion and ferroptosis in trans-differentiating cells.

As a consequence, it has been discovered that instead of component (i) as defined above, an alternative component (iii) may be used; see below. At the same time we note that BCl-2 and the derivatives thereof as disclosed herein can also be viewed as antioxidants in terms of their cellular function.

Accordingly, the first aspect of the invention extends to an alternative method of trans-differentiating differentiated cells. More specifically, provided is a method of trans-differentiating differentiated cells, the method comprising bringing said cells into contact with at least one component (iii) and at least one component (ii), wherein said component (iii) reduces lipid peroxidation and is preferably selected from (a) Vitamin D receptor, a functional homolog thereof, and a nucleic acid encoding said receptor or said homolog thereof; (b) a steroid antioxidant, preferably calcitriol; (c) a phenol antioxidant, preferably a tocopherol or a tocotrienol; and (d) a quinone, preferably coenzyme Q; and wherein said component (ii) is selected from a transcription factor capable of trans-differentiating said cells; a nucleic acid encoding said transcription factor; and means for enhancing the amount and/or activity of said transcription factor in said cells; wherein any method of treatment of the human or animal body by therapy is excluded.

Generally speaking, any agent or compound capable of reducing lipid peroxidation is a suitable component (iii). Preferred agents in that respect are those of items (a), (b), (c) and (d).

Preferably, the vitamin D receptor is a human or murine vitamin D receptor (SEQ ID NOs.: 16 and 17, respectively). Preferably, said homolog of said vitamin D receptor exhibits 80%, 90%, 95% or 98% sequence identity to the sequence of the vitamin D receptor at the amino acid level. A functional homolog is a homolog which preserves the antioxidant function of the vitamin D receptor dependent pathway.

As noted above, a preferred steroid antioxidant in accordance with item (b) is calcitriol, also known as $1\alpha,25(OH)_2$-cholecalciferol or $1\alpha,25(OH)_2$-vitamin D3. Another preferred steroid antioxidant is vitamin D3.

A number of naturally occurring phenols are well-known as antioxidants. A preferred subclass is known as vitamin E. Vitamin E in turn designates a group of compounds. For the present invention, only those members of the vitamin E family are of interest which have antioxidant properties. These include the mentioned tocopherols and tocotrienols. Especially preferred is α-tocopherol.

Quinones are also well-known vitamin-like antioxidant molecules. A preferred quinone is coenzyme Q.

Whenever there is recitation of "at least one component", preference is given to one component. On the other hand, it is understood that the term "at least one" also embraces two, three, four, five or more components, components being component (i), component (ii) or component (iii) as defined herein above.

In a preferred embodiment, the methods of the first aspect are performed in vitro or ex vivo.

The term "in vitro" requires that the method is performed outside the human or animal body in its entirety. The term "in vitro" does not imply any further limitations. It is conceivable that the differentiated cells to be trans-differentiated originate from one organism or species, and the cells obtained as a result of the trans-differentiation process are administered to a different organism or species. The actual steps of obtaining and administering do not fall under the terms of the above defined first aspect.

The term "ex vivo" embraces those implementations, where the differentiated cells to be trans-differentiated are to be taken from one organism, and the cells obtained as a result of the trans-differentiation process are to be re-introduced into the same or different organism. Having said that, it is understood that neither the process of obtaining differentiated cells, nor the process of re-introducing trans-differentiated cells fall under the terms of the first aspect of the invention.

For the sake of completeness, it is noted that the present invention also contemplates a method as defined in accordance with the first aspect, wherein said bringing into contact is preceded by a step of obtaining differentiated cells from a human or animal and/or a step of introducing (in case of ex vivo applications re-introducing) trans-differentiated cells obtained by the method in the same or a different organism. Said different organism may be of the same or a different species. Preferred species are mammals, in particular humans. In the latter case, said method, to the extent it includes a step of introducing trans-differentiated cells, embraces or is confined to therapeutic applications. Medical indications amenable to treatment are further detailed below.

In a second aspect, the present invention provides a combination comprising or consisting of (a) at least one component (i) and at least one component (ii); (b) at least one component (iii) and at least one component (ii); or (c) at least one component (i), at least one component (ii), and at least one component (iii); each of said components being as defined above. For components (i), (ii) and (iii)(a), nucleic acids are preferred.

Said combination may be provided as a single composition of matter, said composition of matter in that case being a mixture. Alternatively, said components and furthermore—to the extent a plurality of either component is used—each of the individual components may be provided separately, for example in a separate vial. In relation thereto, the present invention also provide a kit which is further detailed below. Kits may be designed for in vitro applications, but may also be useful for diagnostic applications (also further detailed below).

Moreover, said combination also has therapeutic applications. Accordingly, the present invention also provides a pharmaceutical composition comprising or consisting of said combination and optionally a pharmaceutically acceptable carrier or excipient. Further, not specified therapeutic agents may also be comprised in a combination or pharmaceutical composition according to the present invention. Preference is given, though, to pharmaceutical compositions which contain only the expressly recited constituents as active agents.

Examples of suitable pharmaceutical carriers, excipients and/or diluents are well known in the art and include phosphate buffered saline, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intrathecal, intraocular, intraperitoneal, subcutaneous, intramuscular, topical, intradermal, intranasal or intrabronchial administration. It is particularly preferred that said administration is carried out by injection. The compositions may also be administered directly to the target site, e.g., by biolistic delivery or delivery by means of a viral vector to an external or internal target site, like a muscle or the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs optionally being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 ng to 10 mg units per kilogram of body weight per minute.

Depending on whether one or more transcription factors are used, different types of trans-differentiated cells will be obtained which in turn may be used for regenerative purposes. Also, said trans-differentiated cells may be generated in situ for therapeutic purposes. Accordingly, the present invention provides, in a fourth aspect, the above defined combination for use in a method of treating or preventing a neuronal or muscular disorder, said neuronal or muscular disorder being characterized by a loss of functional neurons and/or a loss of functional myocytes, wherein said one or more transcription factors are selected from neurogenic and myogenic transcription factors, wherein preferably said treating or preventing is to be effected by trans-differentiating differentiated cells.

Related thereto, the present invention provides the above defined combination for use in a method of treating or preventing a neuronal disorder, said neuronal disorder being characterized by a loss of functional neurons, wherein said one or more transcription factors are selected from neurogenic transcription factors, wherein preferably said treating or preventing is to be effected by trans-differentiating differentiated cells.

Related thereto, the present invention provides the above defined combination for use in a method of treating or preventing a muscular disorder, said muscular disorder being characterized by a loss of functional myocytes, wherein said one or more transcription factors are selected from myogenic transcription factors, wherein preferably said treating or preventing is to be effected by trans-differentiating differentiated cells.

The mentioned loss of functional neurons or loss of functional myocytes may be a partial or complete loss. The term "loss" embraces scenarios where the respective cells are lost as such, for example as a result of apoptosis or necrosis, and furthermore embraces also scenarios where the function of said neurons or myocytes is lost. Functions of neurons include transmission of information. Functions of myocytes include contractility.

In a preferred embodiment (a) said neuronal disorder is selected from neurodegenerative disorders including Alzheimer's disease, Lewy body dementia, Parkinson's disease, epilepsy, and traumatic or ischemic injury of the central nervous system.

In a further preferred embodiment, (b) said muscular disorder is selected from chronic compartment syndrome, Isaac's syndrome, rhabdomyolysis, muscular dystrophy, myasthenia gravis, amyotrophic lateral sclerosis (ALS), multiple sclerosis (MS), Friedrich's ataxia, Lambert-Eaton syndrome, and Kennedy's disease.

In preferred embodiments of the combination according to the second aspect, the pharmaceutical composition according to the third aspect, and the combination for use according to the fourth aspect, the combination or composition, respectively, further comprises in vitro cells amenable to trans-differentiation. Preferred cells amenable to trans-differentiation are fibroblasts including adult human fibroblasts. Also preferred is that said cells amenable to trans-differentiation are autologous cells.

This preferred embodiment does not rely on the presence of cells amenable to trans-differentiation at the site where the combination according to the invention is to be delivered. Instead, cells amenable to trans-differentiation are comprised as a third component in the combination or composition, respectively. Fibroblasts, including mature fibroblasts, are preferred because they are easily accessible.

The present inventors have investigated the functions of Bcl-2 homology domain containing proteins and for the first time clearly disentangled two different functions, said two different functions being apoptosis relevant function on the one hand and trans-differentiation relevant function on the other hand. Accordingly, several preferred embodiments relate to preferred aspects of the polypeptide (component (i)) of the various aspects of the invention as disclosed so far.

In a preferred embodiment, said polypeptide (a) has reduced anti-apoptotic function as compared to human Bcl-2, the amino acid sequence of human Bcl-2 being set forth in SEQ ID NO: 1, or is deprived of its anti-apoptotic function; and/or (b) enhances the yield of trans-differentiated cells to a higher degree than human Bcl-2.

Aspect (a) of this preferred embodiment relates to the present inventors' surprising discovery that anti-apoptotic function, while being a useful criterion for identifying candidate polypeptides, is in fact dispensable. This finding is surprising, given that in the prior art the perception prevails that the anti-apoptotic properties of Bcl-2 family members are key to the putative role of Bcl-2 in differentiation processes.

Anti-apoptotic function may be assayed by standard methods as for example TUNEL assay, DePsipher assay (R&D systems) and staining for propidium iodide and caspase-3 or, alternatively, cell death can be analyzed by time-lapse video-microscopy (see also the methods given in the Examples). Preferably, apoptotic cells are detected and qualified by time-lapse video-microscopy. This allows the direct observation of cell death. Details are given in the methods section of the Examples. As a reference for determining the reduction of anti-apoptotic function, human Bcl-2 consisting of the sequence of SEQ ID NO: 1 can be used. Preferably, the reduction of anti-apoptotic function is at least 10%, at least 20%, at least 30%, at least 40% or at least 50% as compared to human Bcl-2. The term "deprived of its anti-apoptotic function" refers to those mutants which, when using the assay for anti-apoptotic function as described above, do not exert any measurable anti-apoptotic function. As noted above, a reduction of anti-apoptotic function may also be determined by determining an increase of apoptosis. In other words, the above defined polypeptide having reduced anti-apoptotic function as compared to human Bcl-2 at the same time provides for increased apoptosis when used in place of human Bcl-2. Preferably, apoptosis is increased by at least 10%, at least 20%, at least 30%, at least 40%, or at least 50% as compared to human Bcl-2. Presence and degree of apoptosis may be determined by the assays for apoptosis as disclosed herein above.

Having said that, it is also envisaged to maintain the anti-apoptotic function of said polypeptide. In that case, said polypeptide, while enhancing trans-differentiation, will also enhance survival in the course of trans-differentiation. Since in the course of trans-differentiation part of the cells changing cell fate might undergo apoptosis, such enhancing of survival may further enhance the overall yield of the trans-differentiating process of the present invention.

Alternatively or in addition, said polypeptide enhances the yield of trans-differentiated cells to a higher degree than does human Bcl-2. This embodiment relates to another surprising finding of the present inventors. More specifically, said anti-apoptotic function of said polypeptide is not only dispensable. Its reduction or complete abolition even provides for an enhanced capability of trans-differentiating differentiated cells as compared to those polypeptides which, while being embraced by the present invention, still—also—exert anti-apoptotic function. A specific example of such yet further enhanced capability of trans-differentiation is a mutant designated "A Bcl-2" which is further detailed in the Examples enclosed herewith. Enhancement of the yield of trans-differentiated cells as compared to the use of human Bcl-2 can be determined as follows. Differentiated cells, preferably human adult fibroblasts, are brought into contact with a nucleic acid encoding the neurogenic transcription factor Ascl1, wherein said bringing into contact is performed in the presence of human Bcl-2 or in the presence of a candidate polypeptide. Subsequently, the quantity of trans-differentiated cells, in the present case neurons, is counted. If the number of neurons obtained in the presence of the candidate polypeptide exceeds the number of neurons obtained in the presence of human Bcl-2, said candidate polypeptide is a polypeptide which enhances the yield of trans-differentiated cells to a higher degree than does Bcl-2. Preferably, human Bcl-2 consists of the amino acid sequence of SEQ ID NO: 1. Preferably, the number of trans-differentiated cells obtained with the polypeptide in accordance with this preferred embodiment is at least 10%, at least 20%, at least 30%, at least 40% or at least 50% higher than the number of trans-differentiated cells when using human Bcl-2.

In a further preferred embodiment of any of the four aspects of the present invention disclosed so far, said polypeptide is selected from Bcl-2, Bcl-$X_L$, Bcl-w, Mcl1, Bfl1, Nr13/Nrh (Nrh is the human orthologue of Nr13), Bcl2L1, DIVA, myeloid cell leukemia sequence 1 isoform 1, and Bcl-x beta, each preferably being human. The enumerated proteins are well recognized anti-apoptotic proteins with well characterized domain structures. In particular, they comprise at least one domain selected from BH1, BH2, BH3 and BH4 domains. In several instances, they comprise exactly one BH1 domain, exactly one BH2 domain, exactly one BH3 domain, and exactly one BH4 domain. The latter domain structure is particularly preferred. Said proteins may originate from any species, preferably from a mammalian species, and particularly preferred from a human. As noted above, the amino acid sequence of human Bcl-2 (a isoform) is enclosed herewith as SEQ ID NO: 1. The murine counterpart is set forth in SEQ ID NO: 3. The mentioned publications by Inohara et al. set forth the sequence and the domain structure of most of the mentioned proteins.

In a further preferred embodiment, said polypeptide comprises a BH4 domain and optionally one, two, three or more domains selected from the group consisting of a BH1, a BH2, a BH3 and a BH4 domain, and preferably comprises exactly one BH1 domain, exactly one BH2 domain, exactly one BH3 domain and exactly one BH4 domain.

This preferred embodiment defines polypeptides in terms of their domain architecture, the term "architecture" referring to the list of domains occurring in a polypeptide and, in a preferred embodiment, also to the order of domains in said polypeptide. In this regard, we note that while the presence of any one of BH1, BH2, BH3, and BH4 domain is sufficient for qualifying a polypeptide as a candidate polypeptide (which, for being a polypeptide of the invention, needs to pass the above defined trans-differentiation test), the present inventors, without being bound by any specific theory, consider that the presence of a BH4 domain further enhances the likelihood of a structural determinant for trans-differentiation to be present.

As noted above, particularly preferred is the type of domain architecture found in Bcl-2, i.e. the presence of exactly one BH1, exactly one BH2 domain, exactly one BH3 domain and exactly one BH4 domain.

The above defined structural requirement of having a reduced or abrogated anti-apoptotic function has a structural correlate in terms of protein-protein interactions. More specifically, in order to exert its anti-apoptotic function, wild type Bcl-2 interacts with Bax. In a preferred embodiment of any of the above defined aspects of the present invention, said polypeptide does not interact with Bax or the interaction of said polypeptide with Bax is reduced as compared to the interaction of human Bcl-2 with human Bax, the amino acid sequence of human Bax being set forth in SEQ ID NO: 2.

Alternatively, murine Bax may be used in order to determine whether a given polypeptide meets the terms of this preferred embodiment. Murine Bax (amino acid sequence) is provided as SEQ ID NO: 4. Preferably, Bax originating from the same species as the polypeptide of component (i) of the first aspect is used. This also applies to those cases where said polypeptide is a mutant derived from a wild type form. A reduced interaction with Bax in accordance with the present invention requires a reduction of 10%, preferably at least 20%, at least 30%, at least 40%, at least 50% or more of the bound state as compared to the interaction between human Bcl-2 and human Bax. Interaction is preferably determined by means of a biacore assay. Another preferred means of quantifying the interaction between Bcl-2 and Bax is the co-immunoprecipitation assay described in Deng et al. (Molecular and cellular biology 26, 4421-4434 (2006)).

In a further preferred embodiment of any of the aspects of the present invention disclosed above, said polypeptide is selected from a Bcl-2 mutant which (a) differs from wild type Bcl-2 in that one or more phosphorylatable residues in the flexible loop domain are replaced by non-phosphorylatable residues or deleted such as (i) the S70A mutant of human Bcl-2; (ii) the T69A/S70A double mutant of human Bcl-2; (iii) the S87A mutant of human Bcl-2; (iv) the T69A/S70A double mutant of human Bcl-2; (v) the T69A/S87A double mutant of human Bcl-2; (vi) the S70A/S87A double mutant of human Bcl-2; (vii) the T69A/S70A/S87A triple mutant of human Bcl-2; viii) deletion mutants selected from the deletion of one, two or three of T69, S70 and S87 of human Bcl-2; and (ix) the aa 69 to 87 deletion mutant of human Bcl-2; or (b) is a mutant of human Bcl-2 having the transmembrane region deleted or rendered non-functional. Absence or non-functionality of the transmembrane region abrogates membrane association of Bcl-2. Whether a given mutant is membrane-associated or not can be determined by art-established methods, for example by labeling (e.g. with a fluorophor) a candidate mutant and determining its location within the cell.

Subitems (i) to (vii) are replacement mutants. The S70A mutant of human Bcl-2 is also referred to as "A-Bcl-2" herein and is a mutant further characterized in the enclosed examples. The remainder of the replacement mutants shares with this particular mutant the paradigm that one or more residues located in the flexible loop domain and amenable to phosphorylation are replaced by non-phosphorylatable residues. As an alternative to replacement with non-phosphorylatable residues, one or more of said positions may be deleted altogether; see the above subitem (viii). The entire flexible loop domain, preferably amino acid residues 69 to 87 of human Bcl-2 may be deleted. Also, it is envisaged to delete any subregion of said flexible loop domain to the extent at least one of the phosphorylatable residues at positions 69, 70 and 87 is affected by such deletion. The term "flexible loop domain" is established in the art (see Deng et al., Mol. Cell. Biol. 26, 4421 (2006)) and, by reference to human Bcl-2 is defined by the residue range from residue 69 to residue 87 (residues 69 to 84 in murine Bcl-2). In an alternative approach, the transmembrane region, as such a characterizing feature of Bcl-2 wild type (residues 212 to 233 in human, residues 215 to 235 in mouse), may be deleted or rendered non-functional, for example by mutating or deleting one or more residues thereof. Without wishing to be bound by a specific theory, the present inventors believe that their observation that in the course of trans-differentiation Bcl-2 locates to the nucleus, indicates that removal of the transmembrane region may further enhance the trans-differentiation capabilities of polypeptides according to the present invention.

To the extent Bcl-2 sequences originating from other organisms are to be used for the design of corresponding mutants, corresponding amino acids positions can be determined without further ado, for example by means of pairwise or multiple sequence alignment. For the sake of completeness, we note that positions 69, 70 and 87 of human Bcl-2 have their counterparts in positions 69, 70 and 84 of murine Bcl-2.

In a further preferred embodiment of any of the aspects of the present invention disclosed above, the cell is (i) a somatic cell, preferably selected from a fibroblast, an astrocyte, and a pericyte; (ii) of vertebrate, preferably mammalian, more preferably murine or human origin, and/or (iii) from an embryo or a postnatal, preferably adult stage.

In another preferred embodiment, said one or more transcription factors (component (ii)) are selected from neurogenic transcription factors, preferably Ascl1, Neurog2, Dlx2 (Heinrich et al., 2010), Brn2, MYT1L (Vierbuchen et al. (2010), loc. cit.), Sox11 (Liu et al., Nature communications 4, 2183 (2013)) and Sox2 (Karow et al. (2012), loc. cit.) and myogenic transcription factors, preferably MyoD (Choi et al., 1990) (Choi et al., 1990) (Choi et al., 1990) (Choi et al., 1990) (Choi et al., 1990) (Choi et al., 1990) (Choi et al., 1990) (Choi et al., 1990) (Choi et al., 1990) (Choi et al., 1990) (Choi et al., 1990) (Choi et al., Proceedings of the National Academy of Sciences of the United States of America 87, 7988-7992 (1990)), Gata4m, Mef2c and Tbx5 (Ieda et al., Cell 142, 375-386 (2010)), Hand2, T-box5, myocardin, and microRNAs miR-1 and miR-133 (Nam et al., Proceedings of the National Academy of Sciences of the United States of America 110, 5588-5593 (2013)).

In a further preferred embodiment, said cell is a fibroblast, and said one or more transcription factors (i.e. component (ii)) is exactly one transcription factor.

Fibroblasts, while yielding poor amounts of trans-differentiated cells when using prior art methods (typically proceeding via pluripotent state, typically employing complex mixtures of transcription factors) may be used in accordance with the present invention. Fibroblasts are advantageous in view of the easy accessibility.

In a further preferred embodiment, said transcription factor is a neurogenic transcription factor, preferably selected from Ascl1, Neurog2 and Dlx2, and the method yields one or more trans-differentiated cells selected from GABAergic neurons, glutamatergic neurons, and motoneurons. Neurog2 induces glutamatergic neurons, e.g. from astrocytes; Ascl1 and Dlx2 (when used alone or in combination) induce GABAergic neurons from astrocytes; Ascl1 and Neurog2 (when used alone or in combination) induce motorneurons, e.g. from fibroblasts.

In another preferred embodiment, said transcription factor is a myogenic transcription factor, preferably MyoD, and the method yields a muscle cell.

The preceding two preferred embodiments may also be combined, thereby giving rise to another preferred embodiment of the method of the invention, wherein said cell is a fibroblast, and the method comprises the following steps which are to be conducted separately: (a) bringing said fibroblasts into contact with (i) said polypeptide or a nucleic acid encoding said polypeptide, and (ii) exactly one neurogenic transcription factor, preferably selected from Ascl1, Neurog2 and Dlx2, or exactly one myogenic transcription factor, preferably MyoD; (b) bringing the result of step (a), in presence of said polypeptide or a nucleic acid encoding said polypeptide, into contact with exactly one myogenic transcription factor, preferably MyoD in case in step (a) a neurogenic transcription factor has been used, and with exactly one neurogenic transcription factor, preferably either Ascl1 or Neurog2, in case in step (a) a myogenic transcription factor has been used.

It is particularly preferred that said cells, in the course of trans-differentiation, do not go through a pluripotent state. As noted above, the avoidance of a pluripotent state is viewed as an inherent feature of trans-differentiation. The avoidance of a pluripotent state confers distinct advantages in that cells which are potentially tumorigenic are avoided in the course of generating the desired cells.

In another particularly preferred embodiment, one, more or all of said nucleic acid(s) is/are comprised in one or more vector(s). It is particularly preferred to provide both the one or more transcription factors as well as the polypeptide of component (i) of the first aspect in the form of nucleic acids. These nucleic acids may be incorporated in a single vector, or each of them may be incorporated into a separate vector. It is understood that also the provision of a plurality of transcription factors, their coding sequences being comprised in a single vector, is envisaged, wherein the nucleic acid encoding the polypeptide of component (i) of the first aspect of the present invention is provided on a separate vector. Art-established vectors such as MLV-based retroviral vectors, lentiviral vectors and adenoviral based vectors may be used.

In a fifth aspect, the present invention provides a method of generating a model of neuronal and/or muscular disorder, said neuronal or muscular disorder being characterized by a loss of functional neurons and/or a loss of functional myocytes, said method comprising the method of trans-differentiating differentiated cells, wherein a neurogenic and/or a myogenic transcription factor are to be employed as defined above, wherein said fibroblasts have been obtained from an individual having a predisposition for said neuronal and/or muscular disorder or from patient suffering from said neuronal and/or muscular disorder.

This embodiment requires that the cells to be trans-differentiated are obtained from an individual which either suffers from an above defined disorder or has a predisposition to develop such disorder. As a consequence, trans-differentiating fibroblasts will yield neurons and/or myocytes exhibiting phenotypes characteristic of such disorder.

In a sixth aspect, the present invention provides a method of diagnosing a neuronal and/or muscular disorder, said neuronal or muscular disorder being characterized by a loss of functional neurons and/or a loss of functional myocytes, said method comprising the method of trans-differentiating differentiated cells according to the first aspect, to the extent said cell and/or said one or more transcription factors are further defined as herein above, wherein said differentiated cells have been obtained from an individual suspected of having said neuronal and/or muscular disorder or having a predisposition for said neuronal and/or muscular disorder, wherein preferably said differentiated cells are fibroblasts, and wherein a neuron and/or a myocyte as obtained by trans-differentiation and having a diseased phenotype is indicative of said neuronal and/or muscular disorder.

In particular in view of the high efficiency of the method of the first aspect of the present invention, such method of diagnosing may be quicker and/or better than art-established methods of diagnosing a neuronal and/or muscular disorder. An example of a diseased phenotype which can be observed in vitro is the abnormal dystrophin expression in fibroblasts-derived myofibers obtained from patients with Duchenne muscular dystrophy. Expression of dystrophin protein can be analyzed by standard methods such as PCR, Western-blot or immunocytochemistry assays.

In a seventh aspect, the present invention provides a method of producing a composition comprising trans-differentiated cells, wherein said method comprises the method of trans-differentiating differentiated cells as disclosed above.

In a preferred embodiment, no enrichment or purification of trans-differentiated cells is performed. This preferred embodiment takes into account the surprising observation of the present inventors that, when applying the method according to the present invention, a particularly high degree of trans-differentiation as well as an outstanding purity of trans-differentiated cells is obtained.

In a ninth aspect, the present invention provides the use of a polypeptide as defined in accordance with the present invention or a nucleic acid encoding said polypeptide as an enhancer of trans-differentiation, wherein any use in a method of treatment by therapy of a human or animal are excluded.

In a preferred embodiment of the combination in accordance with the second aspect of the present invention, said combination is provided as a kit, wherein components (i) and (ii) of said combination are contained in distinct containers, the kit optionally comprising a manual with instructions for performing the method of the first aspect of the present invention. To the extent more than one transcription factor is to be used, each transcription factor (or vector carrying a nucleic acid encoding a given transcription factor) may be provided in a separate container.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The Figures Show:

FIG. 1. Time-lapse analysis of the effect of Bcl-2 on astrocyte-to-neuron reprogramming.

(A) Epifluorescence images of astroglial cultures transfected with Ascl1/RFP-encoding vector alone (left panels) or in combination with Bcl-2-encoding vector (right panels and insets) where immunoreactivity for β-III-tubulin was tested (lower panels).

(B) Analysis of transfected cells depicted in (A) at different time points.

(C) Examples of still images from video-time lapse movies showing astroglial cells (white arrows), neurons (black arrows) and dying cells (arrowheads) at different time points in cultures transfected with Ascl1/RFP-encoding plasmid alone (left column) or in combination with Bcl-2-encoding vector (right column). Note that the number of neurons is increased by Bcl-2 expression.

(D) Progeny-trees of single cells tracked from example in (C) showing low proliferation during reprogramming, decreased cell death (depicted with "x") in Bcl-2 expressing cells and faster increased conversion into neurons (black lines).

(E) Histogram of the proportion of cells proliferating during 150 h of observation. Note that this ratio is not affected by Bcl-2.

(F) Histogram Quantification of newly trans-differentiated neurons from astroglia expressing Ascl1/RFP alone or in combination with Bcl-2.

(G) Quantification of cell death in astroglia expressing Ascl1/RFP alone or in combination with Bcl-2.

(H) Histogram of astroglia-derived neurons that die during the observation period.

(I) Analysis of neuronal conversion and cell survival during the observation period, of only Ascl1RFP- or Ascl1RFP+Bcl-2-transfected cells. The percentage of neurons is normalized to the initial number of transfected cells at different time-points.

(J) Time distribution of effect of Bcl-2 in Ascl1-mediated astrocyte-neuron trans-differentiation. Note that majority of neurons appear in the first half of the observation period.

Error bars indicate ±SD. *$p<0.05$, **$p<0.01$, $p≥0.05$ no statistically significant difference (n.s.); Mann-Withney-test in E, F, G, H and J; ANOVA Tukeys post-test in I. Scale bars 40 µm.

Figure 2:
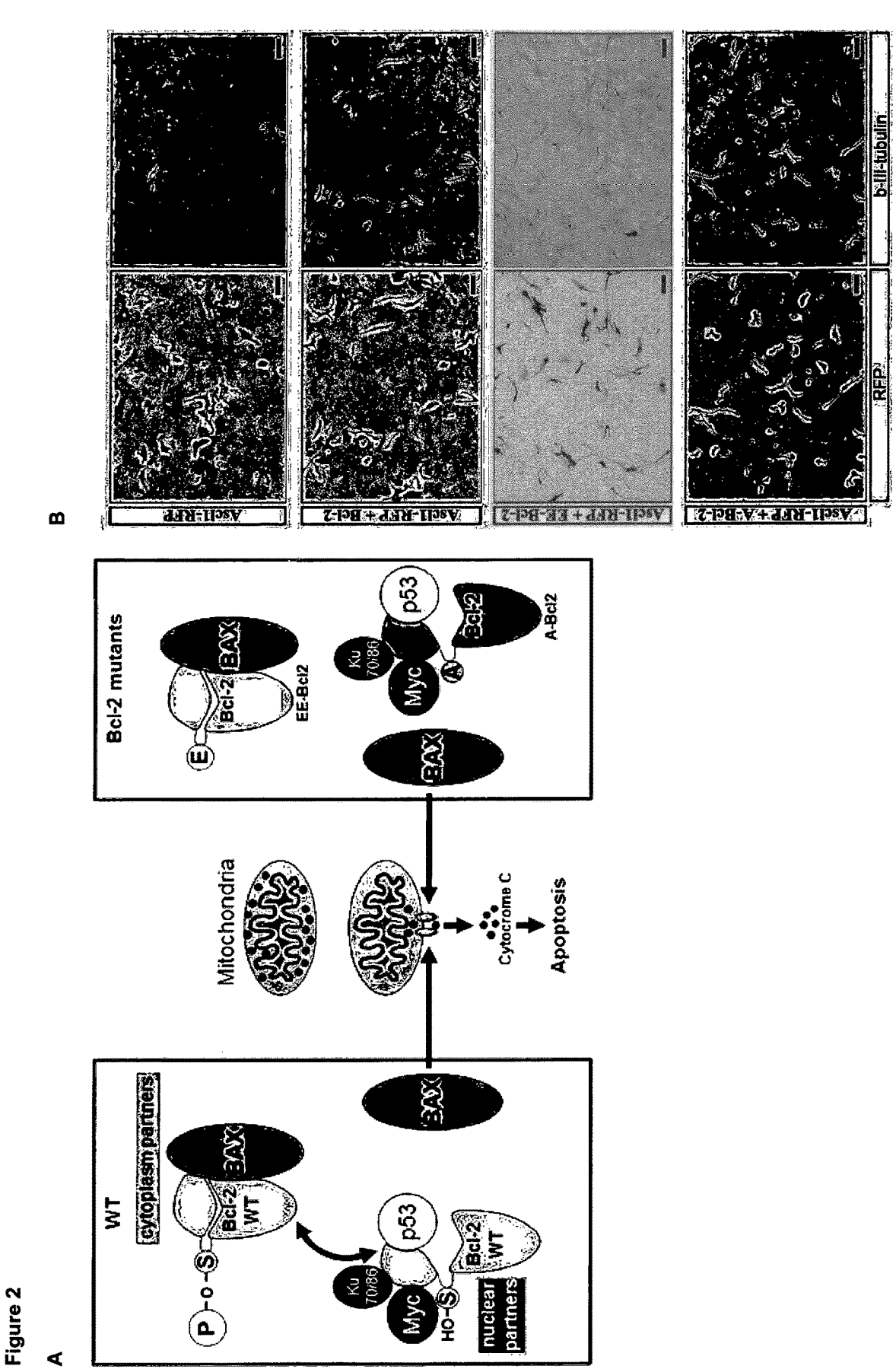
Figure 2:
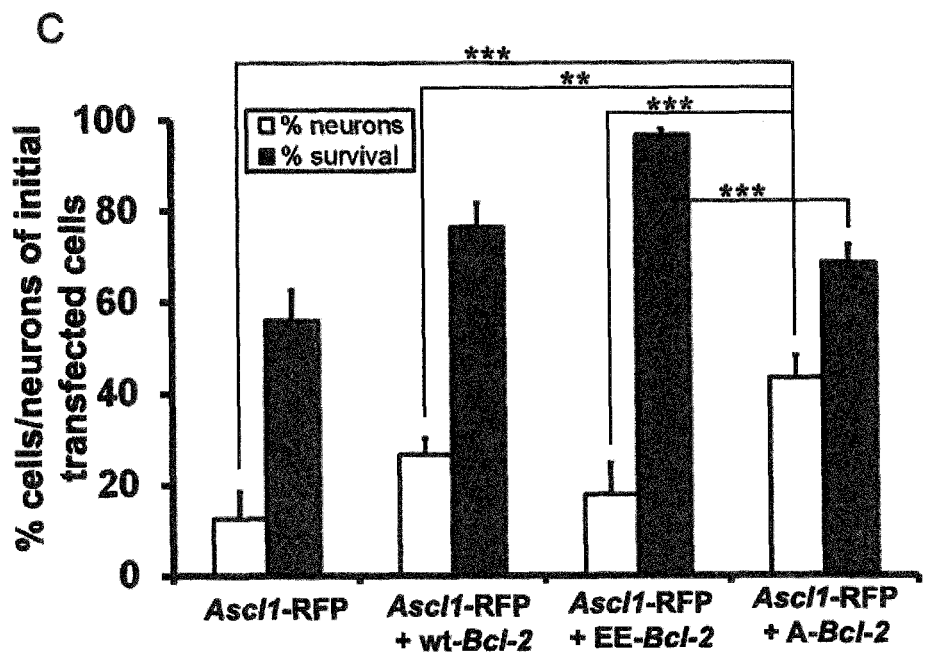

FIG. 2. Effect of Bcl-2 on neuronal reprogramming is independent of interaction with BAX.

(A) Cartoon depicting previously described interactions of Bcl-2 and several molecular partners. Apoptosis mediated by BAX is prevented by interaction with Bcl-2 which occurs when the flexible loop domain of Bcl-2 is phosphorylated at any one of the S70, T69 or S84 (last is S87 of the human BCL-2) positions. Unphosphorylated Bcl-2 binds preferentially to p53 and exhibits a reduced capacity to prevent apoptosis mediated by BAX (Deng et al., Proceedings of the National Academy of Sciences of the United States of America 101, 153-158 (2004)). A-Bcl-2 and EE-Bcl-2 mutants mimic phosphorylated and unphosphorylated configurations of Bcl-2, respectively.

(B) Micrographs of astroglial cultures transfected with Ascl1/RFP-encoding plasmid (left panels) alone ( ) or in combination with Bcl-2, EE-Bcl-2 or A-Bcl-2 at 4 days post transfection. Neuronal conversion was analysed by β-III-tubulin immunostaining (right panels).

(C) Histogram of astroglial cultures transfected with Ascl1-RFP-encoding plasmid alone or in combination with WT-Bcl-2, EE-Bcl-2 or A-Bcl-2 at 4 days post-transfection (DPT). The number of transfected cells (RFP+) at final time point (4 DPT) was normalized to the initial number of transfected cells (1 DPT) to calculate the % of survival. The % of neuronal conversion was analysed by β-III-tubulin immunostaining and normalized to total number of RFP+ cells at the end of the experiment. Error bars indicate ±SD. *$p<0.05$, **$p<0.01$; ANOVA Tukeys post-test. Scale bars 50 µm.

Figure 3:
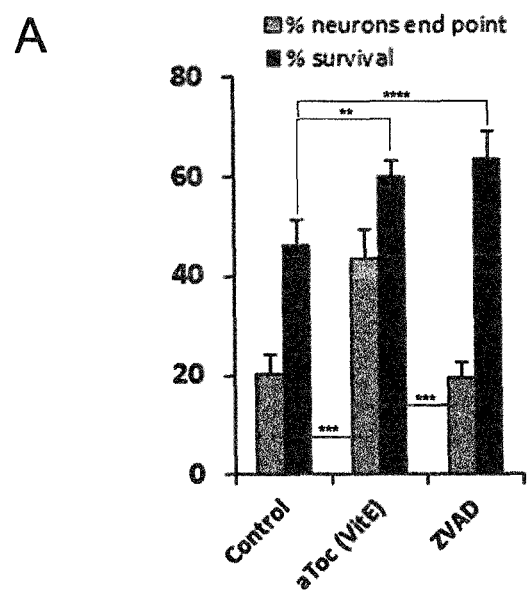
Figure 3:
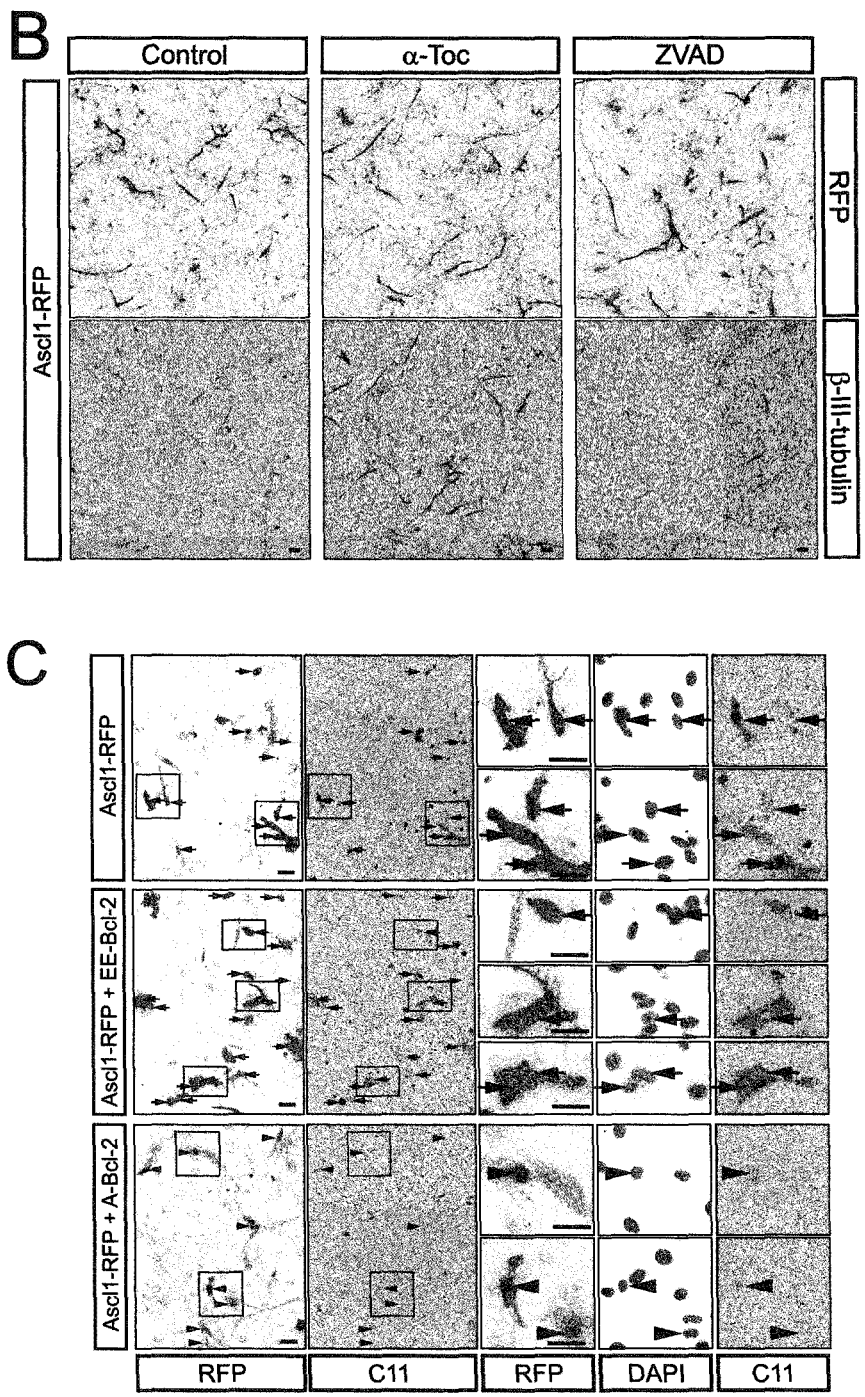
Figure 3:
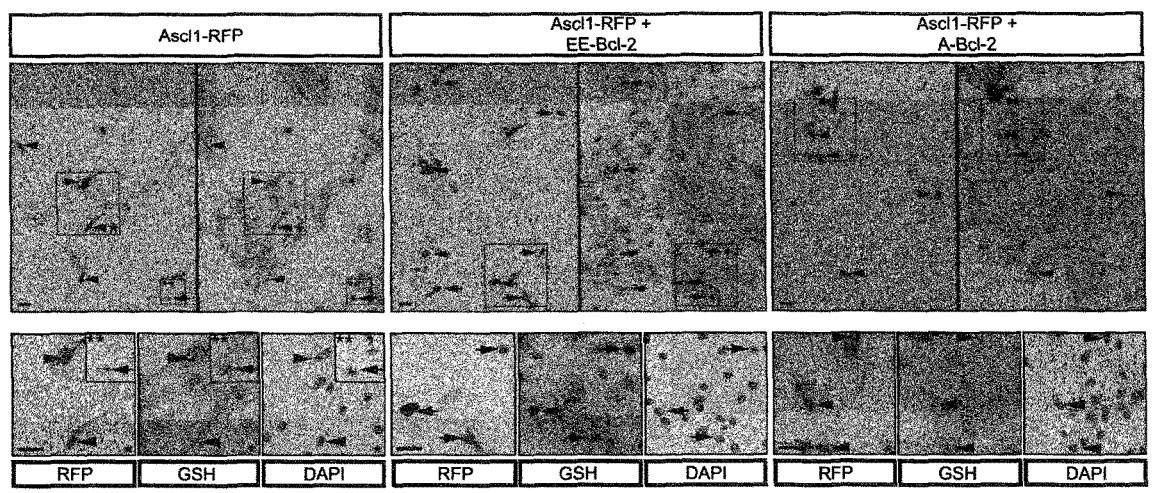

FIG. 3. Reduction of oxidative stress/ferroptosis mediated by Bcl-2 but not apoptosis increases efficiency of neuronal conversion.

A, Quantifications at 5 DPT (days post-transfection) showing the effect of the inhibitor of ferroptosis, α-toc and the inhibitor of apoptosis, ZVAD in survival/efficiency of conversion of astroglial cells transfected with Ascl1-RFP. Note that contrary α-toc, ZVAD improves only survival but not conversion efficiency.

B, Microscope pictures showing examples from A.

C, Micrographs show oxidized lipids (C11-Bodipy staining) at 2 DPT in astroglial cells transfected with Ascl1-REP alone or in combination with EE-Bcl-2 or A-Bcl-2. Note higher levels of oxidation in cells transfected with only Ascl1 or Ascl1+EE-BCl-2 (black arrows) compare to cells co-transfected with Ascl1+A-Bcl-2 (black arrowheads). High magnification pictures show partial co-localization of C11-Bodipy staining and DAPI in Ascl1-expressing cells contrarily to cells co-transfected with Ascl1+EE-Bcl-2 (see arrows).

D, Pictures show glutathione (GSH) detection of same cells shown in C. Cells with normal or increased levels of GSH are depicted by arrowheads and arrows respectively. Higher magnification pictures show that GSH staining is mostly nuclear (see DAPI) in those cells co-transfected with Ascl1-RFP and EE-Bcl-2.

*$p<0.05$, $p<0.01$, *$p<0.001$, $p≥0.05$; ANOVA with Tukey's post-hoc test in A. Scale bars 40 µm.

Figure 4:
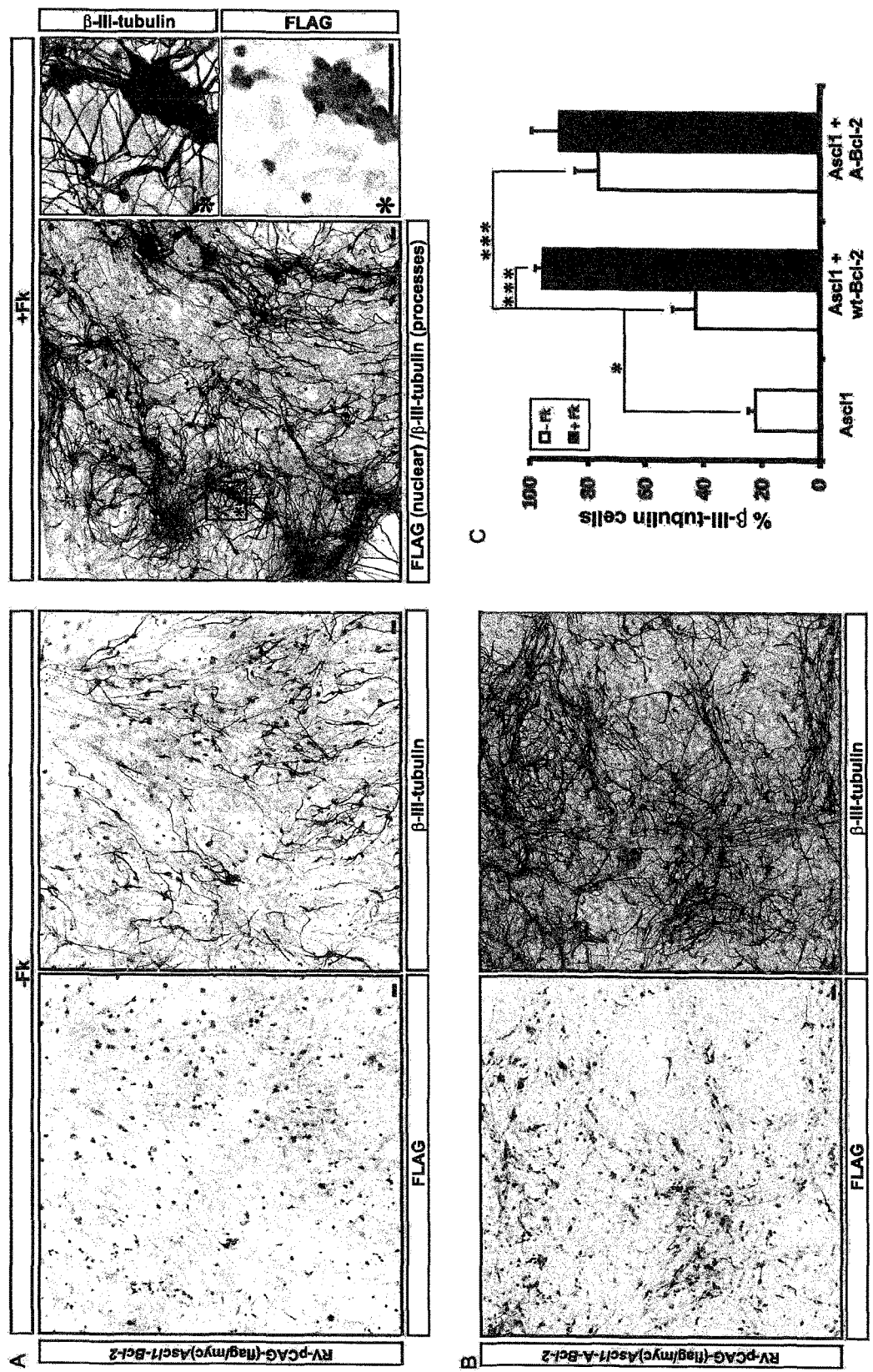
Figure 4:
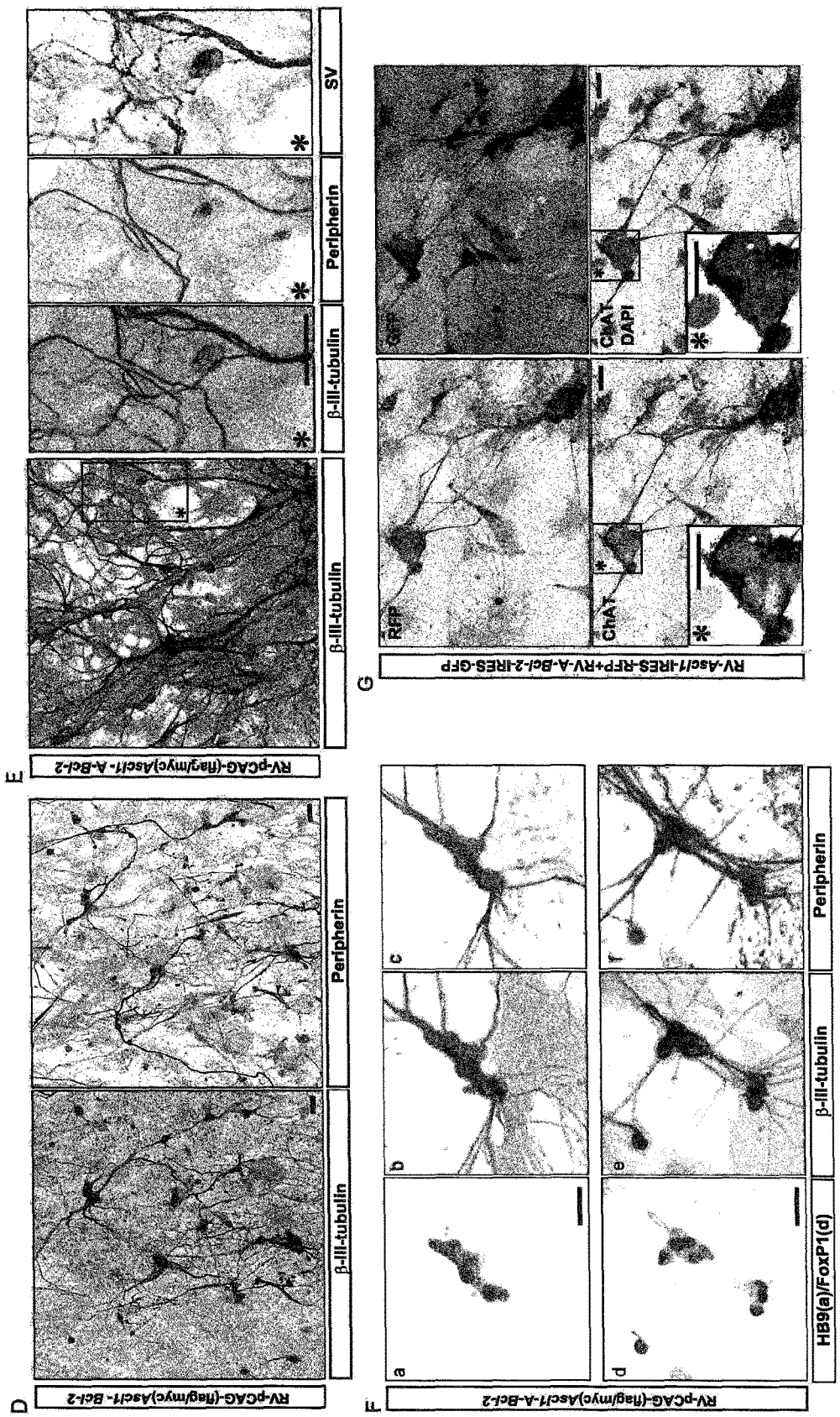

FIG. 4. Bcl-2 and A-Bcl-2 improve Ascl1-mediated conversion of MEFs into motor neurons.

(A) Confocal micrographs of MEFs infected with retrovirus RV-flag/myc-Ascl1-IRES-Bcl-2 showing high proportion of β-III-tubulin immunoreactive neurons among the transduced population 15 days after infection.

(B) Confocal image of MEFs 15 days after infection with retrovirus RV-flag/myc-Ascl1-IRES-A-Bcl-2 named as indicated.

(C) Histogram of the percentage of neurons amongst infected cells. Note that A-Bcl-2 is optimal for inducing Ascl1-mediated trans-differentiation of MEFs into neurons.

(D) Micrograph of MEFs transduced with Ascl1/Bcl-2 co-expressing Peripherin (right panel) and β-III-tubulin (left panel) in neuronal processes.

(E) Micrograph of MEFs transduced with Ascl1/A-Bcl-2 for 20 days demonstrating a complex morphology and co-expressing β-III-tubulin and Peripherin with a high density of Synaptobrevin (SV)-postive puncta.

(F) Micrograph of neurons derived from MEFs transduced with Ascl1/A-Bcl-2 for 15 days positive for HB9 (a), FoxP1 (d), peripherin (c, f) in b-III-tubulin (b, e).

(G) MEFs co-infected with retroviruses expressing Ascl1/RFP and A-Bcl-2/GFP (upper panels) are immunoreactive for ChAT (lower panels) 15 days after infection.

Error bars indicate ±SD. *$p<0.05$, **$p<0.01$; ANOVA Tukeys post-test. Scale bars 30 µm in A, B; 20 µm in D; 25 µm in E; 40 µm in F; 30 µm in G.

Figure 5:
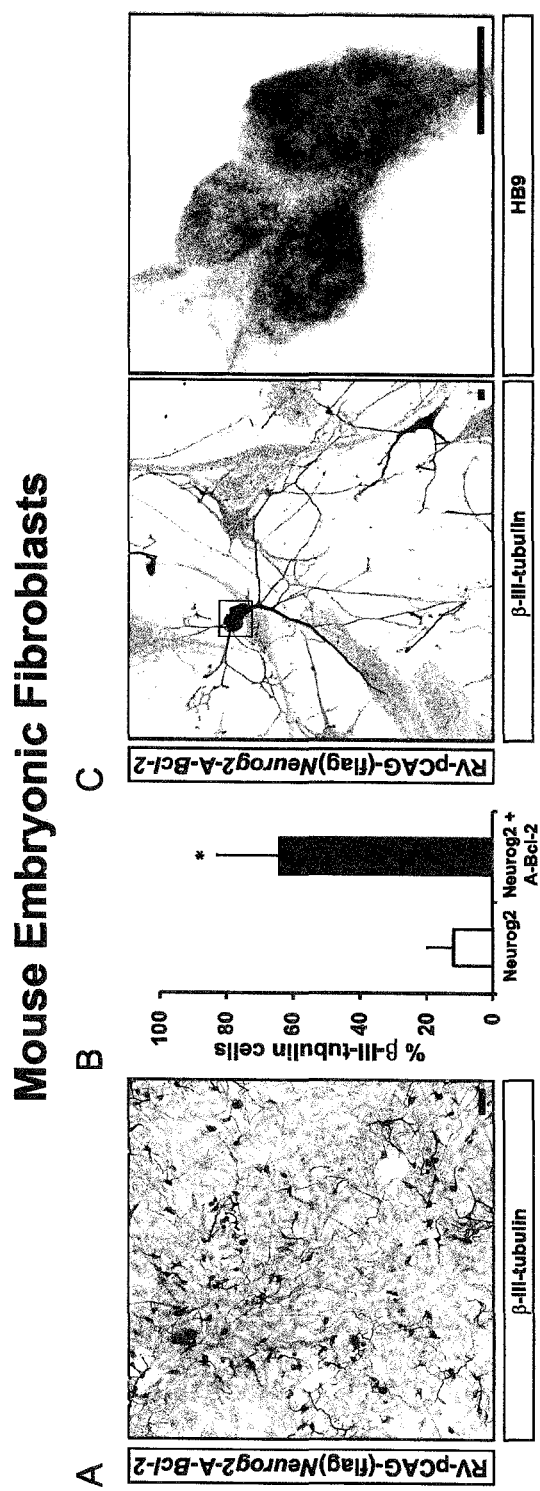
Figure 5:
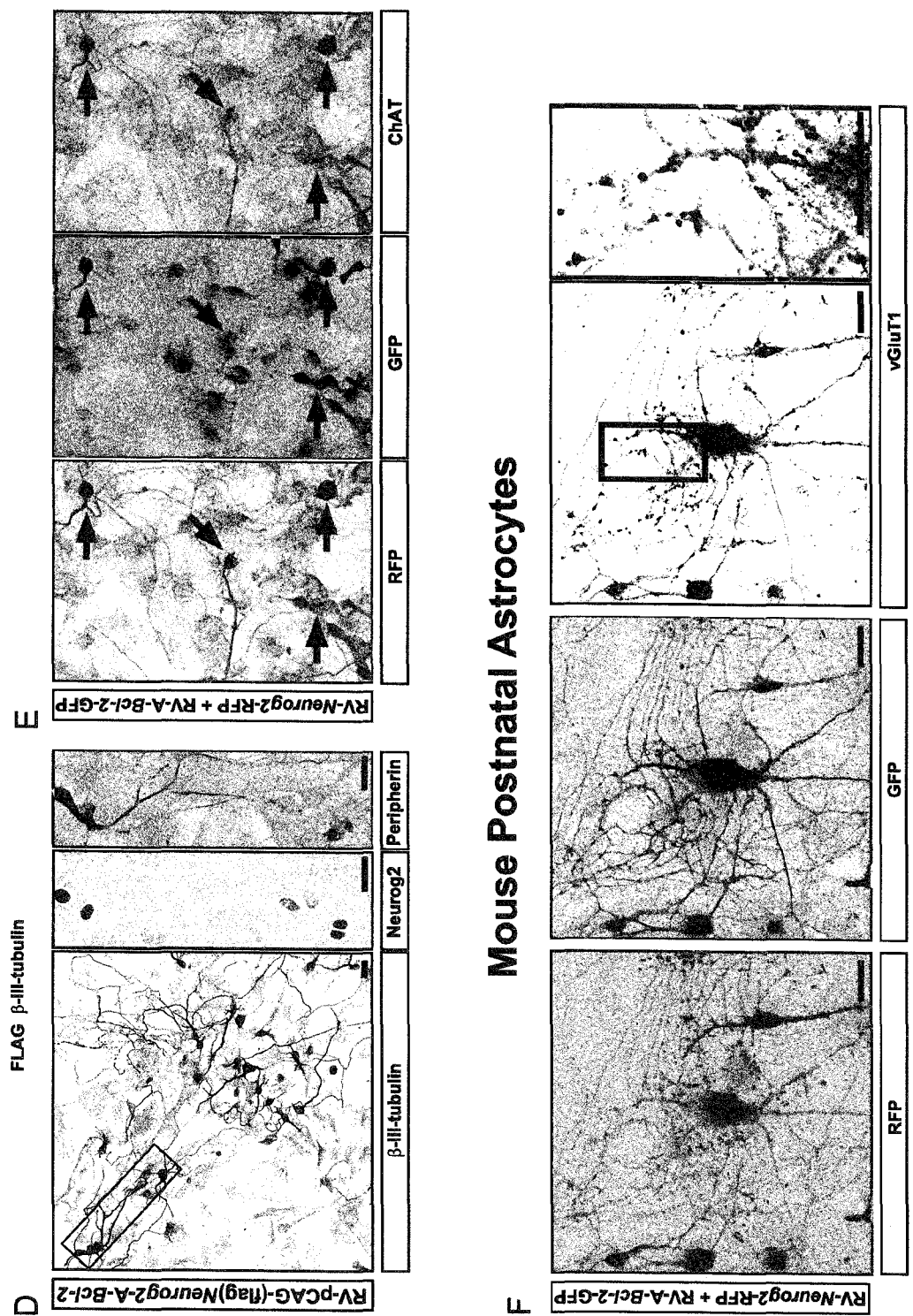

FIG. 5. A-Bcl-2 enhances Neurog2-mediated reprogramming of MEFs into motor neurons and astrocytes into glutamatergic neurons.

(A) Confocal micrograph of MEFs immunostained for β-III-tubulin 15 days after infection with the RV-flag-Neurog2-IRES-ABcl-2. (B) Histogram depicting the proportion of neurons (immunoreactive for β-III-tubulin) amongst all flag+ cells 15 days after infection as exemplified in A and C-E.

(C-E) Micrographs depicting a high magnification of Neurog2-A-Bcl-2 infected MEFs reprogrammed into HB9 immunopositive (see nuclei in inset) motor neurons (C), Flag-immunopositive (inset on left) Neurog2-A-Bcl-2 transduced neurons with long processes immunoreactive for β-III-tubulin and peripherin (inset on right) in (D) and cells co-infected with Neurog2/RFP and A-Bcl-2/GFP (depicted by arrows) immunoreactive for Choline Acetyl Transferase (right panel).

(F) Triple immunostaining for DsRed (left panel), GFP (middle panel), and vGluT1 (right panel and inset) showing that astrocytes derived-neuros induced by Neurog2+A-Bcl-2 are covered by vGluT1-positive puncta, indicative of glutmatergic phenotype.

Error bars indicate ±SD. *p<0.05; Mann-Withney-test. Scale bars represents 40 µm in A and F; 15 µm in C; 20 µm in D and E.

Figure 6:
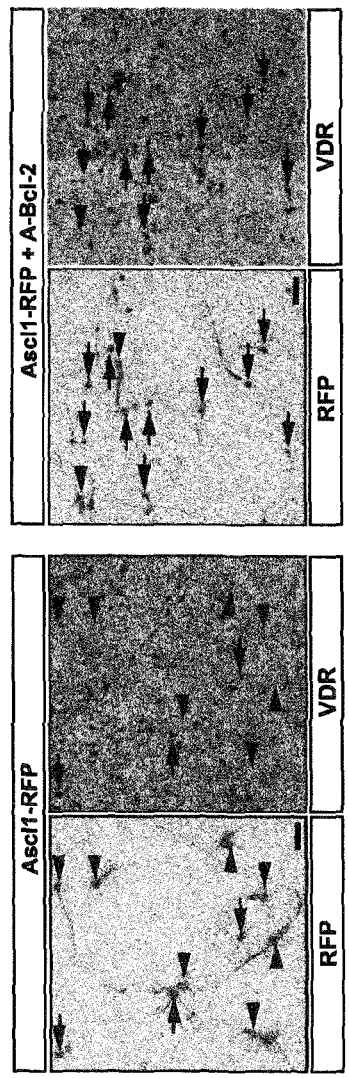
Figure 6:
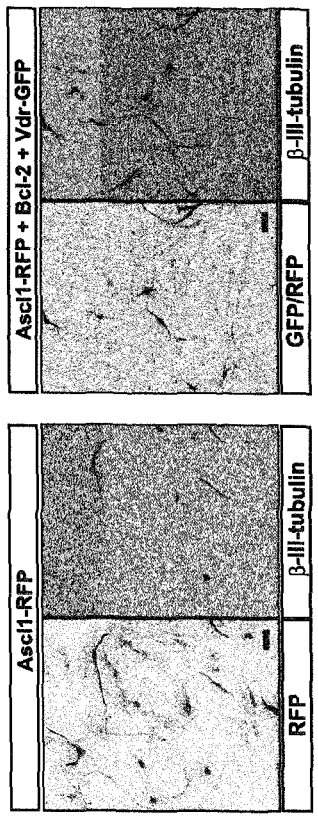
Figure 6:
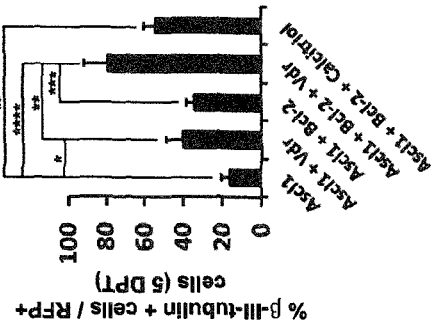
Figure 6:
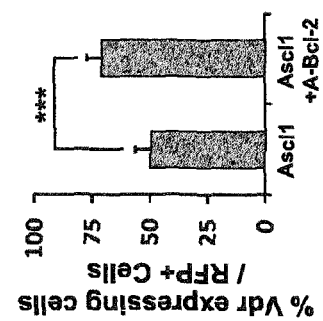
Figure 6:
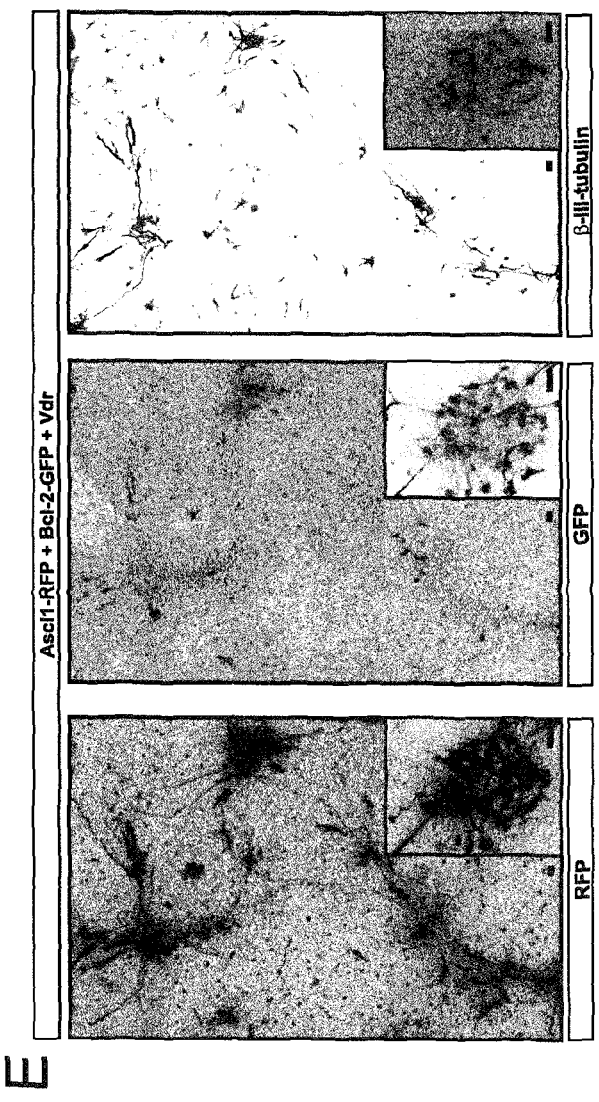

FIG. 6. The role of vitamin D in neuronal conversion.

A, Percentage of cells expressing Vdr in cultures infected with Ascl1-encoding vector alone or Ascl1+A-Bcl-2 at 5 DPI. Vdr presence was determined by immunostaining (B). Note that Bcl-2 increases the proportion of cells expressing endogenous Vdr during neuronal reprogramming.

B, Examples of experiments from A showing the proportion of double RFP+/Vdr+ cells (arrows) and single RFP+/Vdr− cells (arrowheads) in cultures co-transfected with Ascl1-RFP alone (left panels) or in combination with A-Bcl-2 (right panels).

C, Percentage of neurons in astroglial cells transfected with Ascl1-encoding plasmid alone or in combination with Bcl-2 and/or Vdr at 5 DPT after 4 days of treatment with calcitriol or untreated.

D, Examples from the experiments shown in C.

E, Confocal pictures showing neurons obtained from adult human derived fibroblasts (47 age old patient) with the combination Ascl1/Bcl-2/Vdr at 60 DPI. Note that transduced cells extend very long processes. High magnifications (small panels on the bottom) show β-III-tubulin expression in more detail.

*p<0.05, p<0.01, *p<0.001; t test in A; ANOVA with Tukey's post-hoc test in C. Scale bars 40 µm.

Figure 7:
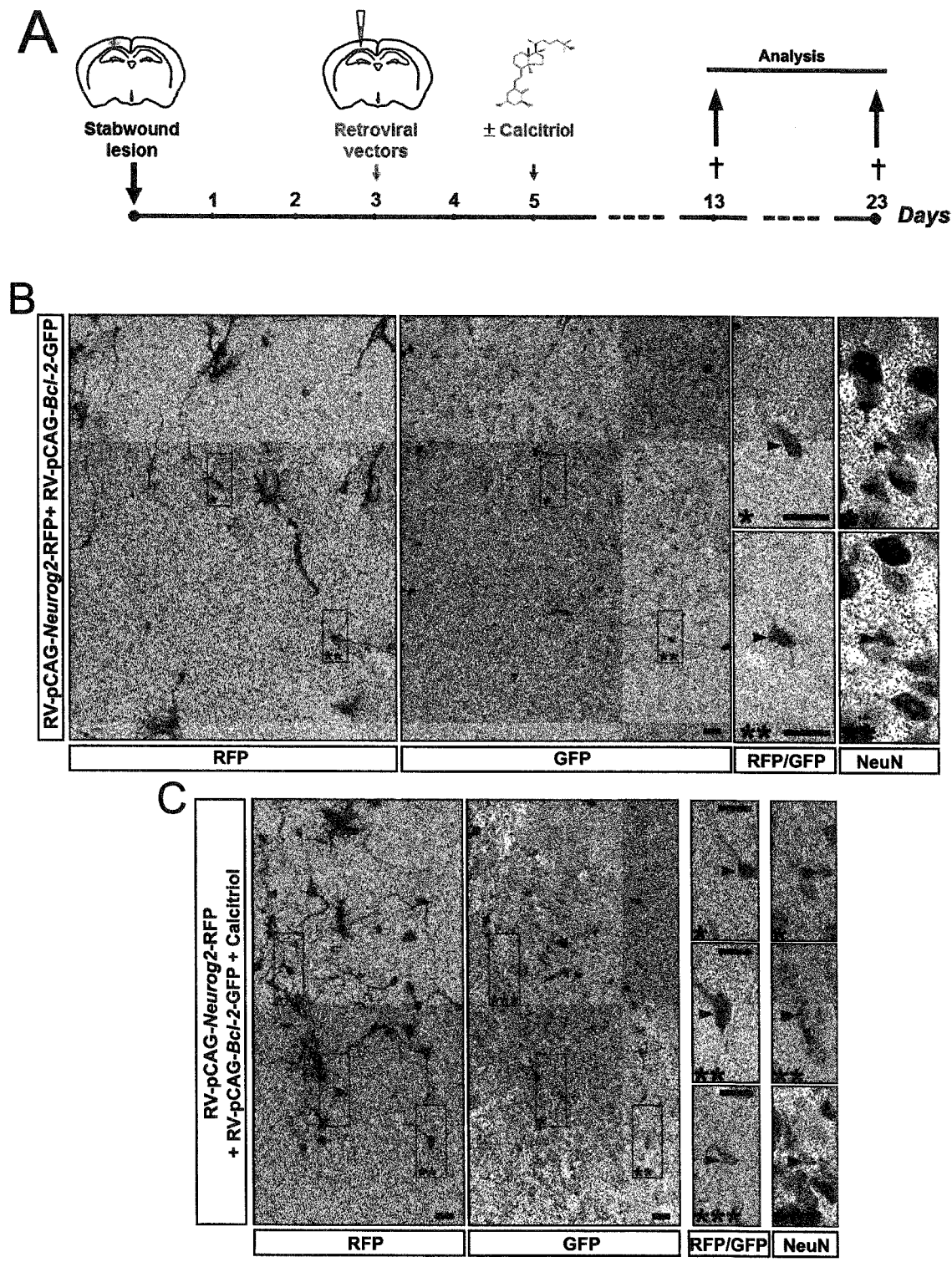
Figure 7:
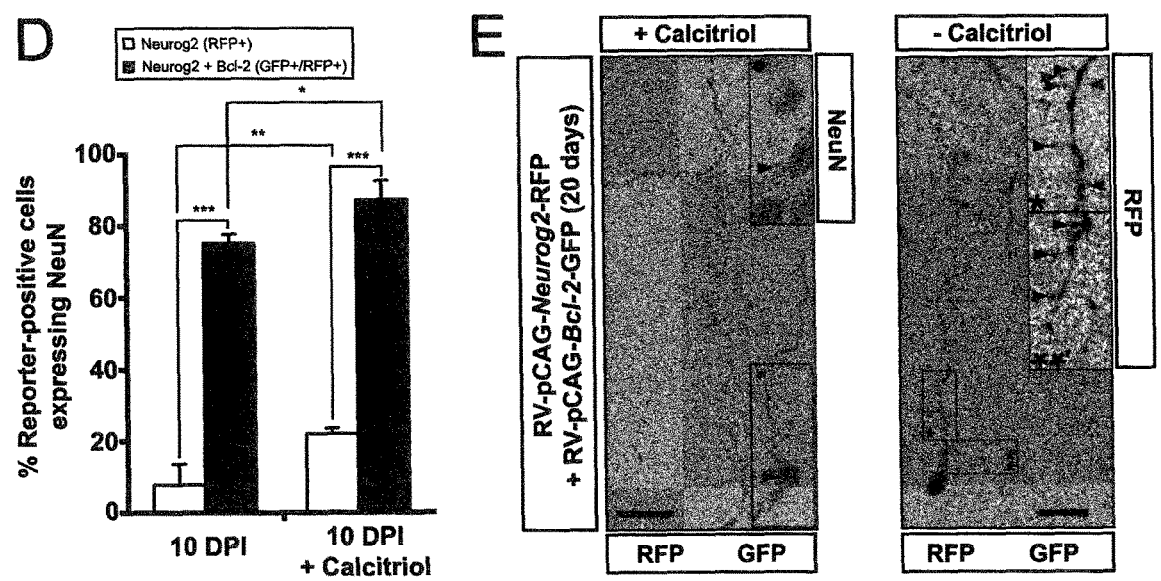

FIG. 7. In vivo conversion of reactive glial cells into neurons with Neurog2, Bcl-2 and calcitriol.

A, Experimental protocol for stab wound injury and subsequent infection with retroviral vectors (Neurog2/RFP and Bcl-2/GFP) or treatment with calcitriol, analysed at 10 or 20 days post-infection (DPI).

B, Confocal picture of the injection site 10 DPI shows cells co-infected with both vectors. White squares (*; **) show higher magnification of single optical sections. Arrowheads indicate NeuN+ (right; white) co-infected cells.

C, Confocal picture of the injection site (10 DPI) after treatment with calcitriol. White boxes (*; ; *) show higher magnification of single optical sections. Arrowheads indicate NeuN+ nuclei of double infected cells. A cell infected only by Neurog2-containing virus (RFP+, arrowhead) expressing NeuN is also shown (').

D, Quantification of RFP+ and RFP+/GFP+ cells that are NeuN+ at 10 DPI, in the absence or in presence of calcitriol. A minimum of three animals has been analyzed for each condition (i.e. with and without calcitriol).

E, Example of co-infected cell at 20 DPI with or without calcitriol administration. The high magnification box (*, left panel) shows the single optical section of the cell soma and the NeuN+ nucleus (arrow). On the right, the white boxes (*; **) show the magnification of two processes with spine-like structures (arrowheads).

*p<0.05, p<0.01, *p<0.001; ANOVA with Tukey's post-hoc test in D. Scale bars 20 µm.

Figure 8:
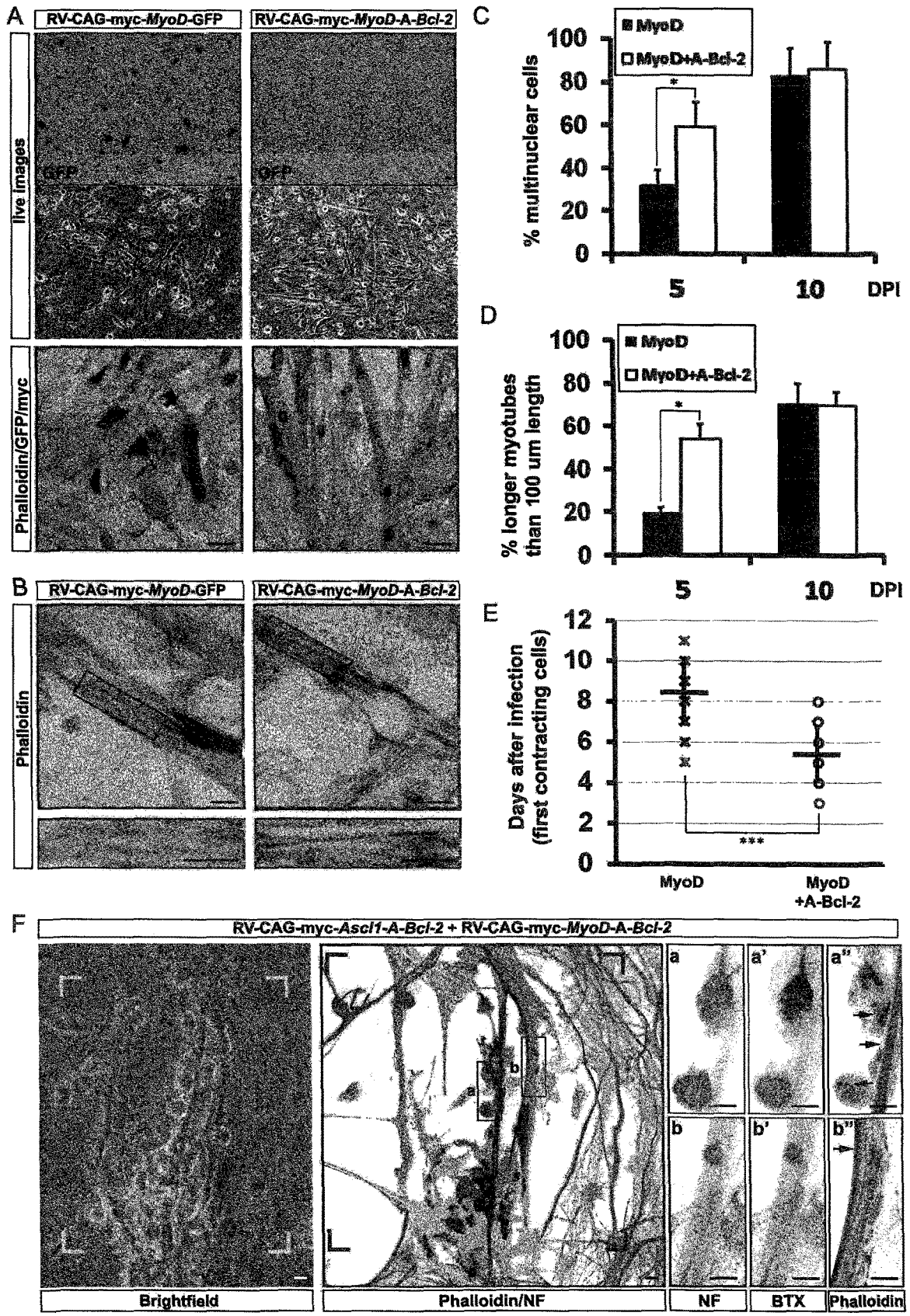

FIG. 8. Co-cultures of reprogrammed motor neurons inervating reprogrammed muscle cells from MEFs.

(A) Live unstained images of MEFs transduced with the retroviral vectors RV-myc-MyoD-IRES-GFP (left panel) and RV-myc-MyoD-IRES-A-Bcl-2 (right panel) revealing increased tubular morphology of A-Bcl-2 expressing muscle cells at 5 days post infection. Lower panels depict morphology of transduced cells immunostained for GFP/myc and additionally stained with phalloidin in fixed cultures.

(B) High magnification confocal images showing an organized structure of sarcomeres in muscle cells co-expressing MyoD and A-Bcl-2 (right panel) compared to the MyoD-expressing controls (left panel) 10 days after infection. See boxed area magnified in lower panels.

(C), (D) and (E) Histograms depicting of muscle cell parameters in MyoD and MyoD/A-Bcl-2 transduced cells. Note that A-Bcl-2 increases the proportion of multinuclear cells (C), myotube length (D) and accelerates contraction ability (E) of MEF-derived muscle cells at 5 DPI.

(F) Micrographs. Immunocytochemistry shows 2 muscles cells stained (middle panel) for phalloidin (darker cells in the center) surrounded by neurofilament-positive (NF; gray cells on the periphery) neurons. White corners mark the same area in brightfield (left panel) and immunostained images. Boxed areas a and b are magnified in panels a-a" and b-b", respectively and reveal connectivity between neurons (NF-positive) and muscle (organized sarcomeres are depicted by arrows) as evidenced by staining for bungarotoxin (BTX).

Error bars indicate ±SD. *p<0.05, **p<0.01; Mann-Withney-test. Scale bars 30 µm in A; 10 µm in B and F.

Figure 9:
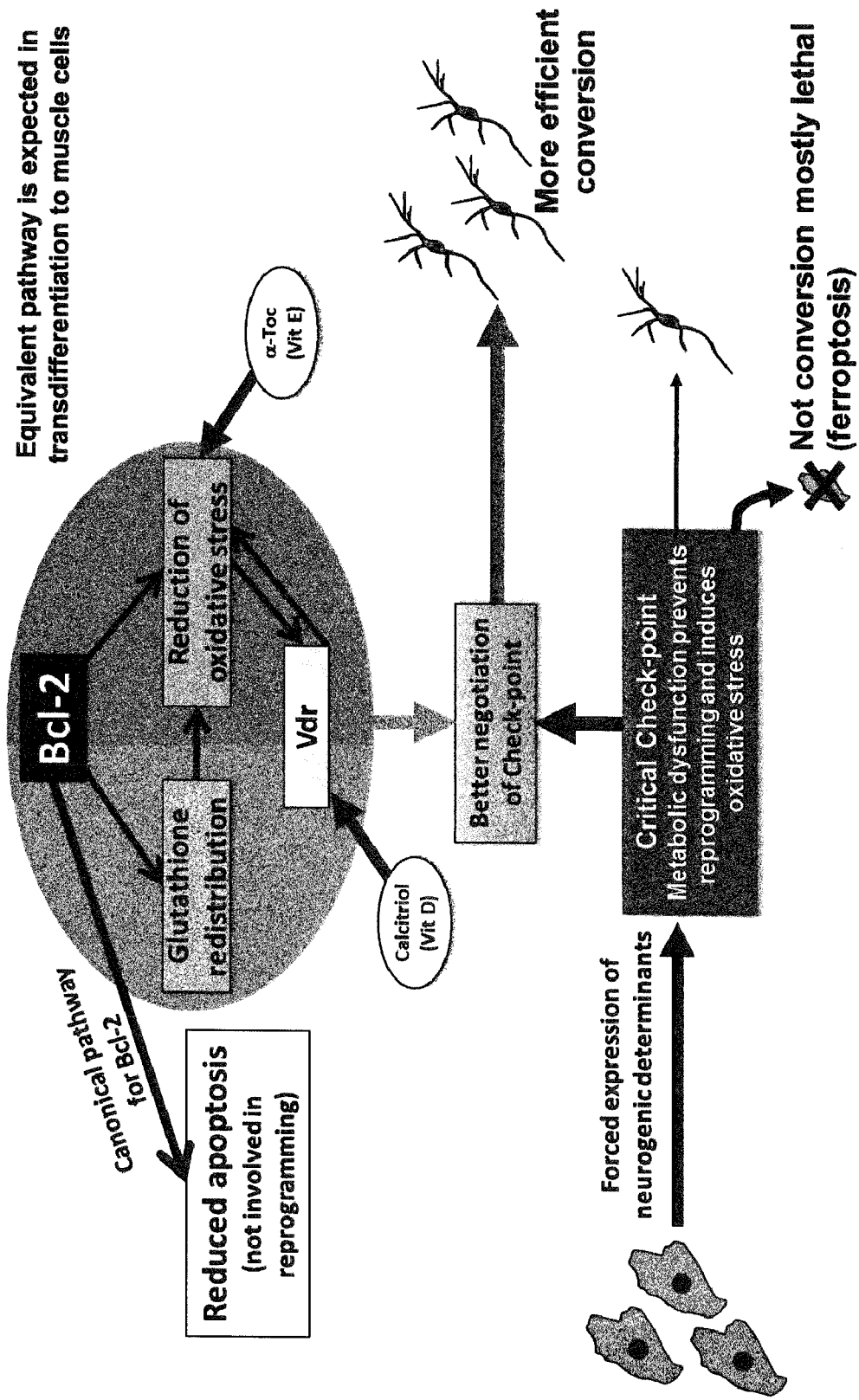

FIG. 9. Schematic drawing summarizing the effects of Bcl-2 in direct reprogramming. As detailed in the text, Bcl-2 expression and other molecular pathways involved in antioxidative stress response such as Vdr enhance neuronal conversion efficiency. Overall, these pathways help to better negotiate a critical check-point in neuronal reprogramming, facilitating transition to a neuronal metabolism and reducing ferroptosis associated to neuronal trans-differentiation. Similar pathways are expected to improve reprogramming of somatic cells into muscle cells.

The Examples illustrate the invention:

EXAMPLE 1

Continuous Single Cell Live Imaging of Direct Neuronal Reprogramming from Astrocytes Reveals a Crucial Role of Cell Death but not Proliferation In order to identify the cellular mechanisms of neuronal reprogramming, astroglia isolated from mouse cerebral cortex at postnatal day 5-7 were transfected with an Ascl1-encoding vector thereby targeting non-proliferating cells in addition to those transduced by approaches such as MLV-based retroviral vectors that require proliferation and breakdown of the nuclear envelope for successful gene transfer. Our transfection protocol (Heinrich et al., PLoS biology 8, e1000373 (2010); Heinrich et al., Nature protocols 6, 214-228 (2011)) enables cells labelled by red fluorescent protein (RFP) 24 hours after transfection to be subject to continuous live imaging for the main phase of reprogramming (i.e. 6 days). Glial and neuronal cells were identified by their morphology, with the former displaying a flat astrocyte-like morphology and the latter with a round cell soma and thin processes (monopolar, bipolar and multipolar) at least 3× longer than the cell soma. This morphology-based classification was confirmed by post-imaging immunostaining (FIG. 1A). Few of the cells transduced with Ascl1 divided during the 150 hours observation (15%: FIG. 1E). Thus, the vast majority of direct neuronal reprogramming occurs in the absence of proliferation in this system.

Conversely, many transduced cells died within the first 100 hours and virtually all transfected glial cells that did not acquire a neuronal morphology succumbed to cell death at some point during the observation period (94±2.4%; FIG. 1G), demonstrating that high expression levels of Ascl1 are not compatible with astrocyte survival, at least under these culture conditions. Interestingly, only around half of the converted neurons died (~48.6%±10.2: FIG. 1H). This indicates that cell lethality during reprogramming is largely restricted to a critical window of 50-100 hours, i.e., during fate conversion and once fate conflicts are resolved in favour of neuronal identity, it significantly declines. Accordingly, most of surviving cells were found to have successfully reprogrammed into neurons. However, this is only around 12% of the initial number of transfected astrocytes (FIG. 1F, I, J). Taken together, selective proliferation plays little role in this paradigm of direct reprogramming, while cell death is a major determinant and peaks at the stages of morphologically visible fate conversion occurring between 50-100 hours during imaging (FIG. 1J).

EXAMPLE 2

Bcl-2 Potently Improves Astrocyte-to-Neuron Conversion

We co-transfected Bcl-2 with Ascl1/RFP in postnatal mouse astrocytes and counted total cells and neuron numbers among the transfected population 6 and 12 days later (FIG. 1A, B). Bcl-2 distinctly increased the total number of surviving cells and reprogrammed neurons (FIG. 1A, B). We performed continuous single cell imaging during reprogramming for 150 hours of astrocytes transduced with Ascl1 only or Ascl1 and Bcl-2. As expected, Bcl-2 co-transduction robustly enhanced survival of cells during neuronal conversion (FIG. 1C-D), but did not alter the specific survival rate of different cell types (FIG. 1G, H). Most strikingly, despite Bcl-2 overexpression the vast majority of cells that failed to convert fate and retained a glial morphology still died (FIG. 1G).

In contrast to the non-converted cells, the rate of cell death was much lower for cells that had successfully acquired a neuronal morphology, with only about ⅓ of these dying (FIG. 1H). Thus, Bcl-2 increased the proportion of cells successfully completing the reprogramming process into neurons by almost 8-fold at 50 h of tracking (FIG. 1F, I) and over 3-fold at the end of the tracking time period (FIGS. 1F, I and J). As successfully converted cells survive with a higher rate (2/3) compared to remaining glial cells (10%), Bcl-2 overexpression resulted in an overall increase in cell survival (FIG. 1B, D, F, I, J). Bcl-2 also accelerated astrocyte-to-neuron conversion, as demonstrated by a significant increase in neurons in the initial phases (the first 50-75 h) of tracking time (FIG. 1I, J). As Bcl-2 did not affect the rate of proliferation during reprogramming (FIG. 1E), its potentiating effects appear to be due to a faster and more efficient conversion of cells to neurons resulting in an increased survival of these cells.

EXAMPLE 3

A Mutant of Bcl-2 Deficient in Interaction with the Pro-Apoptotic Factor Bax Boosts Neuronal Conversion of Astrocytes and MEFs Bcl-2 exerts its survival effect when it is phosphorylated at the positions T69, S70 and/or S87 and changes its conformation such that Phospho-Bcl-2 (P-Bcl-2) binds and sequesters Bax (FIG. 2A) (Deng et al., (2006)); Deng et al., Proceedings of the National Academy of Sciences of the United States of America 101, 153-158 (2004)). As Bax activates caspase-mediated apoptosis by interacting with the mitochondrial membrane and inducing release of cytochrome C (Jurgensmeier et al., Proceedings of the National Academy of Sciences of the United States of America 95, 4997-5002 (1998)), binding of P-Bcl-2 interferes with the Bax-mediated activation of the caspase cascade (FIG. 2A). To specifically decrease the interaction with Bax we used S70A recombinant Bcl-2 (named A-Bcl-2; FIG. 2A) that has a reduced ability to interact with Bax and mimics the un-phosphorylated form of Bcl-2 (Deng et al. (2004)). As a complementary approach, we also used a form of Bcl-2 that mimics the constitutively phosphorylated form of Bcl-2 with increased Bax interaction and pro-survival function by a substitution of both T69 and S70 residues by glutamic acid (T69E+S70E named here as EE-Bcl-2; FIG. 2A; Deng et al., 2004). When WT-Bcl-2, EE-Bcl-2 or A-Bcl-2 were co-transfected with Ascl1-RFP and cell numbers were assessed 4 days later, EE-Bcl-2 strongly increased cell survival during reprogramming as expected (FIG. 2C). Notably, however, contrary to WT-Bcl-2, EE-Bcl-2 failed to significantly increase the proportion of neuronal conversion mediated by Ascl1 (FIG. 2B, D), indicating that augmentation of the pro-survival effect mediated by phosphorylation of the regulatory domain of Bcl-2 interferes with its capacity to boost neuronal reprogramming. Even more intriguingly, when we analyzed cultures co-transfected with the plasmids encoding Ascl1-RFP and the constitutive un-phosphorylated form A-Bcl-2, which exhibits reduced interaction with Bax, we found that the cells showed a decreased survival compared to those transfected with WT-Bcl-2- or EE-Bcl-2-encoding plasmids (FIG. 2C), but an increased proportion of neurons induced from the transfected astrocytes (FIG. 2B, D). Thus, Bcl-2 mediates its effects on reprogramming clearly in its unphosphorylated form and independent of Bax interaction and its pro-survival function. Moreover, Bcl-2 mediates a novel, survival-independent role in neuronal reprogramming.

EXAMPLE 4

Bcl-2 Induces Neuronal Conversion Through Decreasing Oxidative Stress

Some small molecules as α-tocopherol (α-toc; vitamin E) protect from oxidation induced by lipid peroxidation chain reaction in the glutathione peroxidase pathway (Palamanda and Kehrer, 1993) and this is linked to a particular kind of cell death known as ferroptosis (Dixon et al., 2014; Friedmann Angeli et al., 2014; Palamanda and Kehrer, 1993). In the FIG. 3A, B we show that α-tocopherol reduces cell death and increase reprogramming efficiency. This demonstrates that metabolic stress during reprogramming is causative of a reduction in the efficiency of reprogramming and implicates for the first time ferroptosis in the process of reprogramming.

Thus, while ZVAD (FIG. 3A, B) or EE-Bcl-2 (FIG. 2) abolish apoptosis and significantly reduce the percentage of cell death (but not up to 100%) most of these cells are still astrocytes and did not successfully overcome the reprogramming "check-point". Since EE-Bcl-2 and ZVAD do not help to overcome this step, the extra cells that survive will not further go in reprogramming. Therefore, we do not see an increase in induced neurons from the rescued population.

These observations open the question of why EE-Bcl-2 has no effect in neuronal reprogramming while A-Bcl-2 has. For this reason we investigated whether EE-Bcl-2 and A-Bcl-2 exhibit different effects on the cellular accumulation of lipid peroxidation induced by oxidative stress. The data in FIG. 3C (staining with C11-Bodipy) (Drummen et al., 2002) shows that contrary to EE-Bcl-2, A-Bcl-2 is very efficiently reducing oxidative stress. Interestingly we also observed that EE-Bcl-2 strongly induces glutathione transport to the nuclei (FIG. 3D) and this effect was never observed before in this mutant. Since glutathione is required to protect cells from lipid peroxidation and ferroptosis (Dixon and Stockwell, 2014), this result may explain why EE-Bcl-2 is not efficiently reducing metabolic ROS and therefore fails to enhance neuronal reprogramming. Thus, we have identified the mechanism by which A-Bcl-2 is most potent in direct neuronal reprogramming—namely, by reducing ROS—while EE-Bcl-2 fails to do this.

EXAMPLE 5

Ascl1/A-Bcl-2 and Neurog2/A-Bcl-2-Derived Neurons from Fibroblasts Exhibit a Motor Neuron Phenotype Since all the above experiments were performed in postnatal astrocytes, we next asked whether the same effect of Bcl-2 on reprogramming in a Bax-independent manner can also be observed in other models of neuronal reprogramming. As fibroblasts are not as easy to transfect, we generated retroviral vectors encoding for Flag-tagged-Ascl1 and WT-Bcl-2 or A-Bcl-2 (referred to as RV-CAG-Ascl1-IRES-WT-Bcl-2 and RV-CAG-Ascl1-IRES-A-Bcl-2, respectively). Mouse embryonic fibroblasts (MEFs) were infected as described above, and the neuronal conversion was analyzed 14 days later by β-III-tubulin immunostaining. As depicted in FIG. 4A, WT-Bcl-2 doubled the neuronal conversion in MEFs from 22.3% (±2.4) mediated by Ascl1/RFP to 42.8% (±8.1) mediated by Ascl9/WT-Bcl-2 (FIG. 4A, C). Consistent with the results obtained by astrocyte reprogramming, also the efficiency of fibroblast-to-neuron reprogramming could still be further potentiated by A-Bcl-2 (>75%, FIG. 4B, C). As this efficiency exceeds the one of WT-Bcl-2, these results suggest that the proportion of WT-Bcl-2 interacting with Bax at the mitochondrial membrane may not be available for the interaction of Bcl-2 with other partners required for reprogramming. This novel Bax-independent function of Bcl-2 plays a potent role in direct neuronal reprogramming in rather diverse cell types, such as fibroblasts or astrocytes, and is independent of the anti-apoptotic function of Bcl-2.

To further ensure the general role of Bcl-2 in this context we also combined A-Bcl-2 with other reprogramming factors. First, we generated a retroviral vector encoding Neurog2 and A-Bcl-2 (RV-CAG-Neurog2-IRES-A-Bcl-2). Indeed, this combination also increased the proportion of neurons induced from MEFs 6× reaching 63% of all infected cells (compared to 10% mediated by Neurog2/RFP; FIG. 5A, B), demonstrating that the effect of Bcl-2 is transcription factor-independent.

We examined whether Ascl1 may also induce a specific neuronal subtype in murine or human fibroblasts. Indeed, 20 days after viral infection MEFs-derived neurons induced by Ascl1 and Bcl-2 or A-Bcl-2 were immunoreactive for peripherin (FIG. 4D, E), HB9 (also known as MNR2; FIG. 3Fa-c) and ChAT (FIG. 4G) but not for vGluT1 and rarely for vGAT (data not shown), consistent with a motor neuron identity (Aquilonius et al., Brain research 211, 329-340 (1981); Portier et al., Sciences de la vie 316, 1124-1140 (1993); Tanabe et al., Cell 95, 67-80 (1998)) and these peripherin positive processes were covered by dense synaptobrevin-immunopositive puncta indicative of synaptic contacts (FIG. 4E). As these induced neurons also express homogeneously FoxP1 (FIG. 4Fd-f), these appear to be lateral motor column (LMC) and/or preganglionic motor column neurons (Rousso et al., Neuron 59, 226-240 (2008)). Interestingly, MEF-derived neurons induced by the combination of Neurog2 and A-Bcl-2 were also immunoreactive for HB9, peripherin (FIG. 5D) and ChAT (FIG. 5E), but not for Tbr1, Tbr2 or V-Glut (data not shown), characteristic glutamatergic hallmarks (Hevner et al., Neuroscience research 55, 223-233 (2006)). Taken together these data imply that the cell type origin determines the type of neurons induced as Neurog2 induces a glutamatergic neuron identity in astrocytes (See vGluT1 expression in FIG. 5F and Heinrich et al., PLoS biology 8, e1000373 (2010)), while both Neurog2 or Ascl1 induce motor neurons in MEFs.

To determine whether Bcl-2 would also efficiently enhance reprogramming into neurons in cells from other species, we used fibroblasts obtained from a 45 year old female that were expanded and transduced as described above with the retroviral vector encoding Ascl1 and RFP alone or in combination with a second vector encoding the human BCL-2 (hBCL-2) and the reporter GFP. We observed that Ascl1-expression did not induce acquisition of β-III-tubulin immunoreactivity. On the contrary, when the cells were co-transduced with both Ascl1- and hBcl-2-encoding vectors, we observed that up to 70% of the co-infected cells (immunoreactive for RFP and GFP) were β-III-tubulin+(32× fold increase compare to the Ascl1/RFP expressing cells) and acquired neuronal morphology, demonstrating that Bcl-2 has a wide-spread effect potentiating neuronal reprogramming in different cell types and different species. As in the murine counterparts, also the neurons induced from adult human fibroblasts were peripherin- and HB9-immunoreactive motor neurons, suggesting that the motor neuron phenotype is common for all neurons induced from fibroblasts by Ascl1 or Neurog2 without additional neurogenic transcription factors.

EXAMPLE 6

Other Molecules Alleviating Oxidative Stress Downstream to Bcl-2 Also Increase Reprogramming Efficiency Since our previous data demonstrate that oxidative stress is a main hurdle in reprogramming we next tested whether Bcl-2 can regulate expression of other molecules with a known role regulating oxidative stress. One of these molecules is the vitamin d receptor (vdr) which has been previously demonstrated to reduce oxidative stress in several biological paradigms (Bao et al., 2008; Dong et al., 2012). First, we demonstrated for first time that Bcl-2 induces expression of vdr (FIG. 6A, B) and, second, we demonstrated that Vdr over-expression or the application of its ligand calcitriol are also able to enhance reprogramming efficiency of astrocytes (FIG. 6C, D) and human fibroblasts (FIG. 6E). These data are corroborating that oxidative stress is the most important factor preventing neuronal reprogramming and involved Bcl-2 in new pathways inducing vdr expression.

EXAMPLE 7

Bcl-2 and Calcitriol Strongly Enhance Neuronal Reprogramming of Glial Cells In Vivo To highlight the relevance of our findings we next tested the efficiency of the methods described above in vivo. For that, we performed stab wound injury followed by injection of retroviral vectors encoding Neurog2-IRES-RFP and Bcl- 2-IRES-GFP next to the injury site (FIG. 7A) using a previously described protocol (see Heinrich et al., 2014). Control infected cells were glial in nature, mostly NG2+ cells of the oligodendrocyte lineage or S100b/GFAP+ astrocytes as described before (Heinrich et al., 2014). This was also the case for the single GFP+ cells or RFP+ cells (transduced only with Bcl-2 or Neurog2) that rarely acquired the neuronal marker NeuN (FIG. 7B, D). Conversely, many co-transduced cells (GFP+/RFP+) exhibited elongated neuronal-shape morphology and were immunoreactive for NeuN (FIG. 7B, D) and exhibited spine formation (FIG. 7E, right picture), indicative of neuronal conversion. To examine whether key metabolic constraints observed to be important for fate conversion in vitro were also relevant in vivo we tested activation of the Vitamin D receptor pathway by the ligand calcitriol. Calcitriol (200 ng) was administered orally 2 days after viral injection allowing Bcl-2 time to upregulate Vdr. calcitriol treatment increased the proportion of NeuN+ neurons induced by co-expression of Neurog2 and Bcl-2 reaching almost 90% of all co-transduced cells (FIGS. 7C and D), and profoundly improved morphology and maturation state of the neurons, producing long neuronal processes 23 days after viral infection (FIG. 7E, left picture). Overall, these results demonstrate that our findings have a general value in neuronal reprogramming in both in vitro and in vivo paradigms.

EXAMPLE 8

Bcl-2 Also Improves Reprogramming into Muscle Cells and Allows Constructing Neuro-Muscular Junctions Between Induced Neurons and Induced Muscle Cells To determine to which extent Bcl-2 may also foster non-neuronal reprogramming we used retroviral vectors encoding MyoD, a bHLH transcription factor required for myogenic commitment (Braun et al., Development 120, 3083-3092 (1994)) that has been previously determined to induce skeletal muscle conversion from different cell lineages (Choi et al., Proceedings of the National Academy of Sciences of the United States of America 87, 7988-7992 (1990)). When MEFs were infected with RV-CAG-MyoD-IRES-GFP or RV-CAG-MyoD-IRES-A-Bcl-2, MEFs expressing both MyoD and A-Bcl-2 were converted much faster into skeletal muscle cells (FIG. 8A, B). Mature muscle cells were determined by their multinucleated nature and the length of the generated myotubes and significantly more cells acquired a multinuclear myotube morphology (FIGS. 8A, C and D) and more well-organized sarcomeres (FIG. 8B) at 5 DPI after co-infection with A-Bcl-2 compared to the controls expressing only MyoD and the reporter GFP (FIG. 8C, D). Additionally, cultures co-transduced with the MyoD- and A-Bcl-2-encoding vector started to spontaneously contract consistently earlier than the MyoD/GFP transduced controls (FIG. 8E), indicating that A-Bcl-2 also efficiently boosts MEF to muscle conversion. Interestingly, and as observed by time-lapse microscopy for astrocytes, Bcl-2 accelerates fate conversion in this different reprogramming paradigm of turning fibroblasts into myofibers.

Finally we probed the efficiency of Bcl-2 in mediating a functional circuit entirely derived by reprogrammed cells as an easily accessible in vitro model for studying neuro-muscular interactions from direct reprogrammed fibroblasts. For that, MEFs were transduced 4 hours after plating with the vector RV-CAG-Ascl1-IRES-A-Bcl-2 to initiate conversion of MEFs into motor neurons. To avoid undesirable co-infection of different retroviral vectors in the same cell, the cultures were transduced with the second vector RV-CAG-MyoD-IRES-A-Bcl-2 for generation of muscles cells 10 days later, when RV-CAG-Ascl1-IRES-A-Bcl-2 had differentiated into postmitotic neurons and could therefore no longer integrate the RV vector whose integration depends on breakdown of the nuclear membrane during cell division. However, remaining proliferating MEFs could still be infected and were successfully converted into myotubes 7 days later. As expected, we readily found examples of contracting myotubes that later exhibited phalloidin-staining showing well organized sarcomeres and aggregation of nAChRs with affinity for bungarotoxin (BTX) (FIG. 8F), characteristic of neuromuscular junctions. In summary, the potent effects of Bcl-2 in reprogramming allows efficient reprogramming of MEFs into various lineages which can be used to reconstruct functional circuits entirely from directly reprogrammed cells.

EXAMPLE 9

Materials and Methods

Cell Cultures of Astroglia from the Postnatal Mouse Cerebral Cortex

Astrocytes were selected by the culture method described in Heins et al. (Nature Neuroscience 5, 308-315 (2002)). After removal of the meninges, grey matter tissue was dissected from P5-P7 cerebral cortex of C57BL/6J mice and dissociated mechanically. Subsequently, cells were centrifuged for 5 min at 1000 rpm, re-suspended, and plated in medium consisting of DMEM/F12 (Gibco), 3.5 mM glucose (Sigma), 10% fetal calf serum (Gibco), 5% horse serum (Gibco), penicillin/streptomycin (Gibco) and supplemented with B27 (Gibco), 10 ng/mL epidermal growth factor (EGF, Roche) and 10 ng/mL fibroblast growth factor 2 (FGF2, Roche). After one week expansion cells were harvested using trypsin/EDTA (Gibco) and plated onto poly-D-lysine (Sigma-Aldrich) coated glass coverslips in 24-well plates (BD Biosciences) or directly onto the plastic for time lapse experiments at a density of 60,000 cells per well in the same medium. After 24 hours cells were either transfected with plasmid or infected with retroviral vectors and after further 24 hours medium was changed to differentiation medium composed of DMEM/F12 high glucose with GlutaMAX, penicillin/streptomycin and B27 supplement (Gibco) to allow neuronal differentiation.

Cell Cultures of Mouse Embryonic Fibroblasts (MEFs)

MEFs were obtained from mouse embryos at day 14 gestation. Head, spine and visceras were removed and discarded (Vierbuchen et al., Nature 463, 1035-1041 (2010)). The remaining tissue was dissociated with 0.15% of trypsin, centrifuged for 5 min at 1300 rpm, re-suspended, and plated in a medium consisting of DMEM high glucose (3.5 mM) with GlutaMAX (Gibco), 10% fetal calf serum (Gibco) and penicillin/streptomycin (Gibco) in 5% CO2 and normoxygenated conditions. Fibroblasts were used for experiments after minimum 3 passages. For reprogramming experiments cells were harvested and replated as described above for astrocytes.

Transfection of Mouse Postnatal Astroglia Cultures

For transfection DNA-liposome complexes were prepared in Optimem medium (Invitrogen) using the retroviral plasmids described below and Lipofectamine 2000 (Invitrogen). Astrocyte cultures were exposed to DNA-liposome complexes at a concentration of 0.5 µg DNA per 400 µl of Optimem medium for 4 hours and cultured after that in the differentiation medium as above.

Cell Cultures of Mouse Embryonic Fibroblasts (MEFs)

MEFs were obtained from mouse embryos at day 14 gestation. Head, spine and visceras were removed and discarded (Vierbuchen et al., 2010). The remaining tissue was dissociated with 0.15% of trypsin, centrifuged for 5 min at 1300 rpm, re-suspended, and plated in a medium consisting of DMEM high glucose (3.5 mM) with GlutaMAX (Gibco), 10% fetal calf serum (Gibco) and penicillin/streptomycin (Gibco) in 5% CO2 and normoxygenated conditions. Fibroblasts were used for experiments after minimum 3 passages. For reprogramming experiments cells were harvested and replated as described above for astrocytes.

Cell Cultures of Human Fibroblasts

Primary cultures of human skin fibroblasts were established from 3 mm diameter full thickness punch biopsy specimens which were mechanically dissociated before plating. Fibroblasts which grew out from biopsy specimens were maintained and passaged using DMEM (Gibco) with 10% calf serum (Gibco) and penicillin/streptomycin (Gibco) in 5% CO2 and normoxygenated conditions. For reprogramming experiments cells were plated on coverslips in 24-well plates as described above for astrocytes and 48 hours after infection medium was changed to DMEM high glucose with GlutaMAX and 1% fetal calf serum, penicillin/streptomycin and B27 supplement (Gibco). During the reprogramming process, medium was replaced by conditioned-astrocyte medium every 3 days. Conditioned-astrocyte medium is obtained by growing astroglial culture with differentiation medium (see Cell cultures of astroglia from the postnatal mouse cerebral cortex above) during minimum of 2 days. Then the medium is collected from astrocytes and used for reprogramming of the human cells.

Animal Surgery

Operations were performed in accordance with the policies of the state of Bavaria under license number 55.2-1-54-2532-171-11. A unilateral stab wound lesion (1 mm long, 0.6 mm deep from the dura mater) was performed in the right neocortex with a 19 gauge-thick lancet without injuring the cortical white matter, as previously described (Sirko et al. 2013; Simon et al. 2011). Three days later, 0.5-1 µl of retroviral suspension (Neurog2-IRES-RFP and Bcl-2-IRES-GFP, 1:1) was injected in the site of the lesion with a glass capillary connected to a microinjector (Nanoliter2000+Sys-Micro4, World Precision Instrument), at a rate of 30-60 nl/min. The needle was retracted 5 minutes after completing the injection. When indicated in the text, 200 µl of Calcitriol (Tocris) diluted in corn oil (final concentration of 1 ng/µl) were administered through oral gavage 2 days after the retroviral injection. The dosage was determined according with previous publications (Nashold et al. 2013).

Plasmids and DNA Constructs

For the expression of neurogenic transcription factors we used self-inactivating retroviral vectors containing the actin promoter with cytomegalovirus enhancer (pCAG) driving the expression of the gene of interest (flag/myc-Ascl1, flag-Neurog2, Bcl-2 or Dlx-2) linked to a fluorescent reporter by internal ribosomal entry site (IRES) as previously described (Heinrich et al., 2011). The mouse version of Bcl-2 cDNA was obtained from Source BioScience (IRAVp968H01145D; pCMV-SPORT6.1-Bcl-2) and the human cDNA version (h-Bcl-2) from addgene (Plasmid number 8793; pMIG-Bcl-2-IRES-GFP) to generate RV-pCAG-flag/myc-Ascl1-IRES-Bcl-2, RV-pCAG-flag-Neurog2-IRES-Bcl-2 or RV-pCAG-Bcl-2-IRES-GFP, which encodes for both Bcl-2 and the reporter GFP. The Bcl-2 mutants A-Bcl-2 and EE-Bcl-2 were produced by directed mutagenesis with the oligos 5'-ggctgccaggacggctcctctcaggc-ccctcgttg-3' (SEQ ID NO: 18) (and complementary (SEQ ID NO: 20)) and 5'-gggacatggctgccagggaggagcctctcaggc-ccctcgttgcc-3' (SEQ ID NO: 19) (and complementary (SEQ ID NO: 21)) respectively, to generate the vectors pCMV-SPORT6.1-A-Bcl-2, RV-pCAG-Ascl1-IRES-A-Bcl-2 and RV-pCAG-Neurog2-IRES-A-Bcl-2 and the corresponding EE-Bcl-2 versions. Mutations were verified by sequencing. The murine Vdr was obtained from Sino Biological (MG51106-G, Vector pGEM-T) and sub-cloned in the retroviral vector to generate RV-pCAG-Vdr-IRES-GFP.

Viral vectors were produced with a vesicular stomatitis virus pseudotyping at titers of $10^{6-9}$ and cells were infected about 24 hours after splitting as described above. Cells were allowed to differentiate in 16% $O_2$ and 9% $CO_2$.

Immunoblot Analysis

The cultures were lysed in RIPA buffer (10 mM $Na_2HPO_4$, pH 7.2, 150 mM NaCl, 1% sodium deoxicolate, 1% Nonidet P-40, 0.1% SDS) containing protease (Complete EDTA-free, Roche). Protein concentrations were determined with the BCA reagent from Interchim. Equal amounts of protein (50 µg) were separated by polyacrylamide gel electrophoresis and transferred to polyvinylidene difluoride membranes (Pall; Life Sciences).

Immunodetection of proteins was performed by standard procedures (ECL Prime Western Blotting Detection Reagent, Amersham). CREB and P-CREB expression was detected with a polyclonal anti-CREB antibody (Cell Signaling, 48H2) or with a polyclonal anti-P-CREB antibody (S133) (Cell Signaling, 87G3) respectively. PKA phosphorylated targets were detected with polyclonal anti-PKA-substrate (Cell Signaling, 100G7E) and Bcl-2 or α-tubulin with the antibodies polyclonal anti-BCl-2 (Cell Signaling, 50E3) or monoclonal anti-α-tubulin (Sigma, 5168).

Immunocytochemistry

Cells were fixed in 4% paraformaldehyde (PFA) in phosphate-buffered saline (PBS) for 10 min at room temperature (RT), washed in PBS and pretreated in 0.5% Triton X-100 in PBS for 30 min, followed by incubation in 2% BSA and 0.5% Triton X-100 in PBS for 30 min. Primary antibodies were incubated on specimen overnight at 4° C. in 2% BSA, 0.5% Triton X-100 in PBS. The following primary antibodies were used: polyclonal anti-Bcl-2 (Cell Signaling, 50E3), polyclonal anti-P-Creb (S133) (Cell Signaling, 87G3), monoclonal anti-Myc (Cell Signaling, 9B11), polyclonal anti-Green Fluorescent Protein (GFP, chicken, 1:1000, Ayes Labs, GFP-1020), polyclonal anti-Glial Fibrillary Acidic Protein (GFAP, rabbit, 1:4000, DakoCytomation, Z0334), polyclonal anti-Red Fluorescent Protein (RFP, rabbit, 1:500, Chemicon, AB3216, or 1:2000, Rockland 600-401-379), monoclonal anti βIII tubulin (mouse IgG2b, 1:500, Sigma, T8660). After washing in PBS, cells were incubated with appropriate species- or subclass-specific secondary antibodies conjugated to Cy™2, Cy™3, Cy™5 (1:500, Jackson ImmunoResearch), Alexa Fluor 488 (1:500, Invitrogen), FITC (fluorescein isothiocyanate, 1:500, Jackson ImmunoResearch), TRITC (tetramethyl rhodamine isothiocyanate, 1:500, Jackson ImmunoResearch) or biotin (1:500, Jackson ImmunoResearch or Vector Laboratories) or with phalloidin Alexa 594 (Invitrogen, A123819) or bungarotoxin-TRITC (Molecular Probes, T-1175) for 2 h in the dark at room temperature, followed by extensive washing in PBS. Following treatment with secondary antibodies conjugated to biotin, cells were subsequently incubated for 2 h at room temperature with AMCA streptavidin (1:200, Vector Laboratories) or Alexa Fluor 647 streptavidin (1:500, Invitrogen) and mounted with Aqua Poly/Mount (Polysciences, Warrington, Pa.).

For the detection of oxidative stress we used CellROX green Reagent (Life technologies, C10444) according with the described protocol and fluorescence was detected by microscope (see below).

Immunohistochemistry

Animals were anesthetized and transcardially perfused with 1× phosphate-buffered saline (PBS), followed by 4% paraformaldehyde (PFA) in PBS. Brains were postfixed for 2 hours, washed twice with PBS and embedded in 4% agarose/water. Finally, 60 µm-thick coronal sections were cut using a vibrating microtome (Leica).

For immunohistology, sections were pre-incubated for 30 min in blocking solution (2% bovine serum albumin, 0.5% Triton X-100 in PBS). The following primary antibodies were diluted in blocking solution and incubated with the sections for 48 hours at 4° C.: chick anti-GFP (1:500, Ayes Labs, GFP-1020), rabbit anti-RFP (1:500, Rockland, 600-401-379), mouse anti-NeuN (1:250, Chemicon, MAB377). After washing in PBS, secondary antibodies were diluted in blocking solution and incubated at room temperature for 2 hours. They were chosen according to the primary ones and were coupled to Alexa Fluor 488 or FITC, Cy3, Alexa Fluor 647. Sections were eventually counterstained with DAPI (Sigma Aldrich) prior to mounting.

RNA Extraction and Real Time Quantitative PCR (qRT-PCR)

RNA was extracted using RNeasy Plus Micro Kit (Qiagen) according to manufacturer's instructions, including removal of genomic DNA. RNA was retro-transcribed using SuperScriptIII Reverse Transcriptase and Random Primers (Roche). Each cDNA sample was diluted one to 5 and 1 µl was used for each quantitative real time reaction. Real Time quantitative PCR (qPCR) was performed on a LightCycler480 instrument (Roche) using LightCycler Probe Master kit (Roche) and Monocolor Hydrolysis Probe (UPL) Probe (Roche) according to manufacturer's instructions (20 µl final volume). The expression of each gene was analyzed in triplicate. Data were processed with the $\Delta\Delta$Ct method (Livak and Schmittgen, 2001). Quantification was performed on 3 independent samples.

Microscopy

Immuno-stainings were analyzed with a LSM710 laser-scanning confocal or Axio Observer Z1 epifluorescence microscope (Carl Zeiss). Digital images were captured using the ZEN software (Carl Zeiss) and cell counts of all RFP/GFP immunoreactive cells performed with a 10× objective.

Live Imaging Microscopy

Time-lapse video microscopy was performed with a cell observer (Zeiss) at a constant temperature of 37° C. and 8% CO2. Phase contrast images were acquired every 5 minutes, and fluorescence pictures every 4-6 hours for 6.5-7.5 days using a 10× phase contrast objective (Zeiss), and an Axio-CamHRm camera with a self-written VBA module remote controlling Zeiss AxioVision 4.7 software (Rieger and Schroeder, Journal of cellular biochemistry 108, 343-352 (2009)). Movies were assembled using Image J 1.42q (National Institute of Health, USA) software and are played at speed of 3 frames per second.

Statistics

Statistical analyses were performed with GraphPrism 4 software by using Man-Withney or ANOVA Tukeys post-tests. Either all the transfected cells from 3 coverslips were counted for each experiment with at least 3 independent experimental batches. Retroviral vector-transduced cells were quantified from five randomly chosen 10× fields in 3 different wells for each experiment in at least 3 independent experiments.

FURTHER REFERENCES

Bao, B. Y., Ting, H. J., Hsu, J. W., and Lee, Y. F. (2008). Protective role of 1 alpha, 25-dihydroxyvitamin D3 against oxidative stress in nonmalignant human prostate epithelial cells. International journal of cancer Journal international du cancer 122, 2699-2706.

Choi, J., Costa, M. L., Mermelstein, C. S., Chagas, C., Holtzer, S., and Holtzer, H. (1990). MyoD converts primary dermal fibroblasts, chondroblasts, smooth muscle, and retinal pigmented epithelial cells into striated mononucleated myoblasts and multinucleated myotubes. Proceedings of the National Academy of Sciences of the United States of America 87, 7988-7992.

Dixon, S. J., Patel, D. N., Welsch, M., Skouta, R., Lee, E. D., Hayano, M., Thomas, A. G., Gleason, C. E., Tatonetti, N. P., Slusher, B. S., et al. (2014). Pharmacological inhibition of cystine-glutamate exchange induces endoplasmic reticulum stress and ferroptosis. eLife 3, e02523.

Dixon, S. J., and Stockwell, B. R. (2014). The role of iron and reactive oxygen species in cell death. Nature chemical biology 10, 9-17.

Dong, J., Wong, S. L., Lau, C. W., Lee, H. K., Ng, C. F., Zhang, L., Yao, X., Chen, Z. Y., Vanhoutte, P. M., and Huang, Y. (2012). Calcitriol protects renovascular function in hypertension by down-regulating angiotensin II type 1 receptors and reducing oxidative stress. European heart journal 33, 2980-2990.

Drummen, G. P., van Liebergen, L. C., Op den Kamp, J. A., and Post, J. A. (2002). C11-BODIPY(581/591), an oxidation-sensitive fluorescent lipid peroxidation probe: (micro)spectroscopic characterization and validation of methodology. Free radical biology & medicine 33, 473-490.

Friedmann Angeli, J. P., Schneider, M., Proneth, B., Tyurina, Y. Y., Tyurin, V. A., Hammond, V. J., Herbach, N., Aichler, M., Walch, A., Eggenhofer, E., at al. (2014). Inactivation of the ferroptosis regulator Gpx4 triggers acute renal failure in mice. Nature cell biology 16, 1180-1191.

Heinrich, C., Bergami, M., Gascon, S., Lepier, A., Vigano, F., Dimou, L., Sutor, B., Berninger, B., and Gotz, M. (2014). Sox2-Mediated Conversion of NG2 Glia into Induced Neurons in the Injured Adult Cerebral Cortex. Stem cell reports 3, 1000-1014.

Heinrich, C., Blum, R., Gascon, S., Masserdotti, G., Tripathi, P., Sanchez, R., Tiedt, S., Schroeder, T., Gotz, M., and Berninger, B. (2010). Directing astroglia from the cerebral cortex into subtype specific functional neurons. PLoS biology 8, e1000373.

Heinrich, C., Gascon, S., Masserdotti, G., Lepier, A., Sanchez, R., Simon-Ebert, T., Schroeder, T., Gotz, M., and Berninger, B. (2011). Generation of subtype-specific neurons from postnatal astroglia of the mouse cerebral cortex. Nature protocols 6, 214-228.

Livak, K. J., and Schmittgen, T. D. (2001). Analysis of relative gene expression data using real-time quantitative PCR and the 2(-Delta Delta C(T)) Method. Methods 25, 402-408.

Palamanda, J. R., and Kehrer, J. P. (1993). Involvement of vitamin E and protein thiols in the inhibition of microsomal lipid peroxidation by glutathione. Lipids 28, 427-431.

Vierbuchen, T., Ostermeier, A., Pang, Z. P., Kokubu, Y., Sudhof, T. C., and Wernig, M. (2010). Direct conversion of fibroblasts to functional neurons by defined factors. Nature 463, 1035-1041.

The invention claimed is:

1. A method of trans-differentiating differentiated cells selected from fibroblasts and astrocytes into neurons, the method comprising contacting or introducing into said differentiated cells at least one component (i) and at least one component (ii), wherein said component (i) is selected from group consisting of:

(a) a polypeptide of the Bcl-2 family, said polypeptide of the Bcl-2 family being selected from the group consisting of: human Bcl-2 having the sequence of SEQ ID NO: 1, human Bcl-2 having the sequence of SEQ ID NO: 5, and murine Bcl-2 having the sequence of SEQ ID NO: 3; a nucleic acid encoding said polypeptide; or forskolin at a concentration that enhances the amount and/or activity of said polypeptide in said differentiated cells;

(b) a polypeptide comprising the amino acid sequence of a wild-type form of a member of the Bcl-2 family or a fragment thereof, said wild-type form of a member of the Bcl-2 family being selected from the group consisting of: human Bcl-2 having the sequence of SEQ ID NO: 1, human Bcl-2 having the sequence of SEQ ID NO: 5, murine Bcl-2 having the sequence of SEQ ID NO: 3, and human Bcl-$X_L$ having the sequence of SEQ ID NO: 6, wherein the fragment has at least 98% sequence identity with the wild-type form and wherein said wild-type form has anti-apoptotic activity; a nucleic acid encoding said polypeptide; or a forskolin at a concentration that enhances the amount and/or activity of said polypeptide in said differentiated cells;

(c) a polypeptide comprising the amino acid sequence of a wild-type form of a member of the Bcl-2 family or a fragment thereof, said wild-type form of a member of the Bcl-2 family being selected from the group consisting of: human Bcl-2 having the sequence of SEQ ID NO: 1, human Bcl-2 having the sequence of SEQ ID NO: 5, murine Bcl-2 having the sequence of SEQ ID NO: 3, and human Bcl-$X_L$ having the sequence of SEQ ID NO: 6, wherein said polypeptide comprises one or more point mutations as compared to said wild-type form or fragment thereof, wherein the fragment has at least 98% sequence identity with the wild-type form, wherein said wild-type form has anti-apoptotic activity, wherein one or more phosphorylatable residues in a flexible loop domain are replaced by non-phosphorylatable residues in said polypeptide; or forskolin at a concentration that enhances the amount and/or activity of said polypeptide in said differentiated cells; and (d) a polypeptide comprising an amino acid sequence which exhibits at least 98% sequence identity with a wild-type form of a member of the Bcl-2 family, wherein said wild-type form has anti-apoptotic activity, said wild-type form of a member of the Bcl-2 family being selected from the group consisting of: human Bcl-2 having the sequence of SEQ ID NO: 1, human Bcl-2 having the sequence of SEQ ID NO: 5, murine Bcl-2 having the sequence of SEQ ID NO: 3, and human Bcl-$X_L$ having the sequence of SEQ ID NO: 6, wherein one or more phosphorylatable residues in a flexible loop domain are replaced by non-phosphorylatable residues in said polypeptide; a nucleic acid encoding said polypeptide; or forskolin at a concentration that enhances the amount and/or activity of said polypeptide in said differentiated cells;

wherein said component (i) enhances the yield of neurons by at least 30% as compared to the absence of said component (i); and wherein said component (ii) is one or more neurogenic transcription factors, said transcription factors being Ascl1 and/or Neurog2.

2. The method of claim 1, further comprising contacting or introducing into said differentiated cells at least one component (iii), wherein component (iii) reduces lipid peroxidation and is selected from the group consisting of:
   (a) vitamin D receptor, a functional homolog thereof, or a nucleic acid encoding said receptor or said homolog thereof;
   (b) a steroid antioxidant;
   (c) a phenol antioxidant; and
   (d) a quinine.

3. The method of claim 1, wherein said polypeptide as defined in (b), (c), or (d) has reduced anti-apoptotic function as compared to said human Bcl-2 of (a); and/or wherein said polypeptide as defined in (b), (c), or (d) enhances the yield of neurons to a greater degree than said human Bcl-2 of (a).

4. The method of claim 1, wherein said polypeptide as defined in (c) or (d) of claim 1 is selected from a Bcl-2 mutant which
   (a) differs from wild type Bcl-2 in that one or more phosphorylatable residues in the flexible loop domain are replaced by non-phosphorylatable residues or deleted, the Bcl-2 mutant being selected from
      (i) the S70A mutant of human Bcl-2;
      (ii) the T69A/S70A double mutant of human Bcl-2;
      (iii) the S87A mutant of human Bcl-2;
      (iv) the T69A/S70A double mutant of human Bcl-2;
      (v) the T69A/S87A double mutant of human Bcl-2;
      (vi) the S70A/S87A double mutant of human Bcl-2;
      (vii) the T69A/S70A/S87A triple mutant of human Bcl-2;
      (viii) deletion mutants selected from the deletion of one, two or three of T69, S70 and S87 of human Bcl-2; and
      (ix) the aa 69 to 87 deletion mutant of human Bcl-2; or
   (b) is a mutant of human Bcl-2 having the transmembrane region deleted or rendered non-functional,
   wherein human Bcl-2 has the sequence set forth in SEQ ID NO: 1 or 5.

5. The method of claim 1, wherein said differentiated cells are (i) of vertebrate origin; and/or (ii) from an embryonic- or post-natal stage.

6. The method of claim 5, wherein said differentiated cells are fibroblasts.

7. The method of claim 6, wherein said one or more neurogenic transcription factors are Ascl1 and Neurog 2 and the method yields one or more neurons selected from the group consisting of inhibitory neurons, excitatory neurons, and cholinergic neurons.

8. The method of claim 7, wherein the one or more trans-differentiated cells are selected from GABAergic neurons, glutamatergic neurons, and motor neurons.

* * * * *